US 010179858B2

United States Patent
Shintou et al.

(10) Patent No.: US 10,179,858 B2
(45) Date of Patent: Jan. 15, 2019

(54) COMPOUND, INK, RESIST COMPOSITION FOR COLOR FILTER, THERMAL TRANSFER RECORDING SHEET, AND TONER

(71) Applicant: CANON KABUSHIKI KAISHA, Tokyo (JP)

(72) Inventors: Taichi Shintou, Saitama (JP); Koromo Shirota, Kawasaki (JP); Yuko Katsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/763,783

(22) PCT Filed: Aug. 12, 2016

(86) PCT No.: PCT/JP2016/003725
§ 371 (c)(1),
(2) Date: Mar. 27, 2018

(87) PCT Pub. No.: WO2017/056372
PCT Pub. Date: Apr. 6, 2017

(65) Prior Publication Data
US 2018/0273757 A1    Sep. 27, 2018

(30) Foreign Application Priority Data

Sep. 30, 2015  (JP) .................. 2015-194474

(51) Int. Cl.
*G03G 9/09*    (2006.01)
*C09B 23/06*   (2006.01)
(Continued)

(52) U.S. Cl.
CPC .......... *C09B 23/06* (2013.01); *B41M 5/3854* (2013.01); *B41M 5/39* (2013.01); *C09D 11/03* (2013.01);
(Continued)

(58) Field of Classification Search
CPC .......... G03G 9/09; G03G 9/0906; G03G 9/12; G03G 9/122
See application file for complete search history.

(56) References Cited

U.S. PATENT DOCUMENTS

| 5,580,980 A | 12/1996 | Etzbach et al. |
| 6,528,223 B1 | 3/2003 | Wilson et al. |

(Continued)

FOREIGN PATENT DOCUMENTS

| JP | 05-262062 A | 10/1993 |
| JP | 2014-062241 A | 4/2014 |

(Continued)

*Primary Examiner* — Hoa V Le
(74) *Attorney, Agent, or Firm* — Canon U.S.A.Inc., IP Division

(57) ABSTRACT

The present invention provides a compound having a high chroma and also excellent dispersibility. The compound described above is represented by the following formula (1).

General Formula (1)

[Chemical structure showing a compound with substituents $R_1$, $R_2$, $R_3$, $R_4$, $R_5$, and $(R_6)_n$, including a thiazole ring, a pyridone ring with CN group, and a phenyl ring]

6 Claims, 1 Drawing Sheet

(51) Int. Cl.
  *C09D 11/03* (2014.01)
  *G02B 5/22* (2006.01)
  *B41M 5/385* (2006.01)
  *B41M 5/39* (2006.01)
  *G03G 9/087* (2006.01)

(52) U.S. Cl.
  CPC ......... *G02B 5/223* (2013.01); *G03G 9/08755* (2013.01); *G03G 9/0924* (2013.01); *B41M 2205/30* (2013.01)

(56) References Cited

U.S. PATENT DOCUMENTS

| | | |
|---|---|---|
| 2014/0158956 A1 | 6/2014 | Shintou |
| 2014/0170552 A1 | 6/2014 | Shintou |
| 2015/0232678 A1 | 8/2015 | Okubo |

FOREIGN PATENT DOCUMENTS

| | | |
|---|---|---|
| JP | 2014-062242 A | 4/2014 |
| JP | 2014-063155 A | 4/2014 |
| JP | 2014063156 A | 4/2014 |
| WO | 92/19684 A1 | 11/1992 |
| WO | 2015129371 A1 | 9/2015 |
| WO | 22015129373 A1 | 9/2015 |

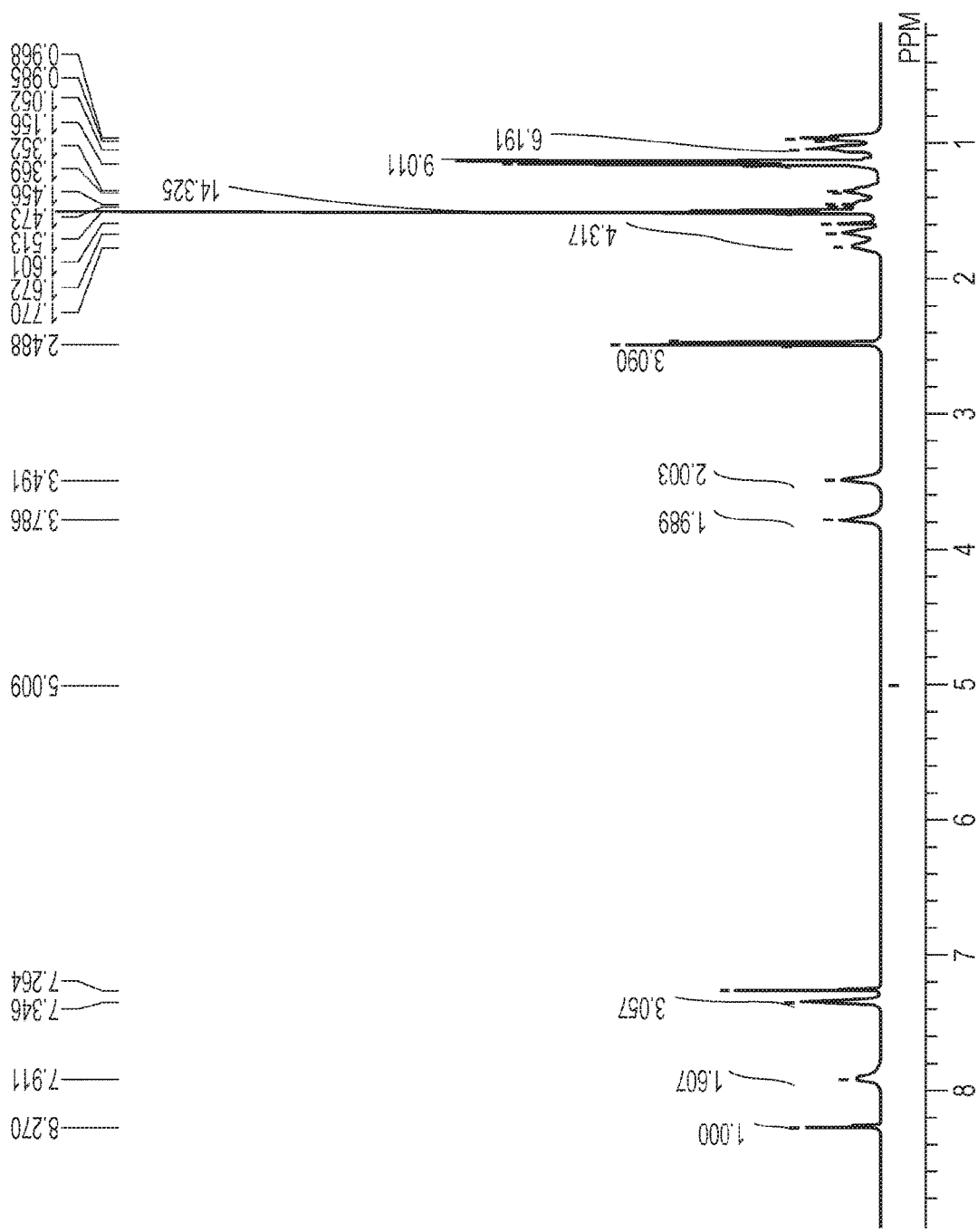

COMPOUND, INK, RESIST COMPOSITION FOR COLOR FILTER, THERMAL TRANSFER RECORDING SHEET, AND TONER

CROSS-REFERENCE TO RELATED APPLICATIONS

This application is a National Stage filing of International Application No. PCT/JP2016/003725 filed Aug. 12, 2016, which claims the benefit of Japanese Patent Application No. 2015-194474, filed Sep. 30, 2015, the disclosures of each of which are hereby incorporated by reference herein in their entirety.

TECHNICAL FIELD

The present invention relates to a compound and to an ink, a resist composition for a color filter, a thermal transfer recording sheet, and a toner, each of which uses the compound described above.

BACKGROUND ART

In a color display using a liquid crystal, a color filter is used. The color filter is an essential component for a color display of a liquid crystal display and is also an important component determining the performance thereof. As a manufacturing method of a related color filter, a dying method, a printing method, an ink jet method, and a photoresist method have been known. Among those methods mentioned above, a photoresist method has been primarily used since the spectral characteristics and the color reproducibility can be easily controlled, the resolution is high, and a more highly minute pattern can be formed.

In manufacturing of a color filter using a photoresist method, in general, a pigment has been used as a colorant. However, a color filter using a pigment have many problems, such as a depolarization effect (destruction of polarization), a decrease in contrast ratio of a color display of a liquid crystal display, a decrease in lightness of a color filter, and a decrease in dispersion stability to an organic solvent or a polymer. Accordingly, a manufacturing method using a dye as a colorant has drawn attention. In PTL 1 and PTL 2, a color filter using a methine-based dye as a colorant has been reported.

In addition, in recent years, with the spread of a mobile color display device, easy color printing of photos and documents, each of which is photographed, processed, and/or further formed using the device mentioned above, has been increasingly in demand.

As a color printing method, for example, an electrophotographic method, an ink jet method, and a thermal transfer recording method have been known. Among those methods mentioned above, since printing can be performed by a dry process, and the printer is compact and excellent in mobility, a thermal transfer recording method is superior as a method in which printing can be easily performed regardless of use environments. In the thermal transfer recording method, a dye contained in a transfer sheet and an ink composition therefor is a very important material since influencing the speed of transfer recording, the image quality of a recorded material, and the storage stability. In PTL 3 and PTL 4, as one example of a dye to be used for a thermal transfer recording method, a methine-based coloring material excellent in clearness, color reproducibility, color density, and the like has been reported.

In addition, in the field of a color toner used in an electrophotographic method, in order to improve the chromogenic property, there has also been reported an example in which instead of using a pigment which has been used in the past, a dye is used as a colorant. Furthermore, in recent years, digital textile printing using an ink jet method has again drawn attention as a method capable of providing a textile printed product at a low energy and a low cost. As an ink jet ink for textiles, although a pigment may be used in some cases, in order to improve the chromogenic property, an example using a dye has been reported. In PTL 5 and PTL 6, as a colorant for a toner, examples using an azo-based dye and a methine-based dye have been disclosed.

Since the dye compounds disclosed in the documents described above each have many hydrogen bonding substituents in its molecule, in all types of applications, there has been a problem in that the dye compound is liable to aggregate by the intermolecular interaction under a high concentration condition. Hence, development of a compound capable of suppressing the intermolecular aggregation even under a high concentration condition has been desired.

CITATION LIST

Patent Literature

PTL 1: Japanese Patent Laid-Open No. 2014-62241
PTL 2: Japanese Patent Laid-Open No. 2014-62242
PTL 3: International Publication No. 92/19684
PTL 4: Japanese Patent Laid-Open No. 05-262062
PTL 5: Japanese Patent Laid-Open No. 2014-63155
PTL 6: Japanese Patent Laid-Open No. 2014-63156

SUMMARY OF INVENTION

The present invention provides a compound having a high chroma and also excellent dispersibility even under a high concentration condition. In addition, by the use of the compound described above, the present invention also provides an ink, a resist composition for a color filter, a thermal transfer recording sheet, and a toner, each of which has a high chroma and also excellent dispersibility even under a high concentration condition.

The present invention relates to a compound represented by the following general formula (1).

[Chem. 1]

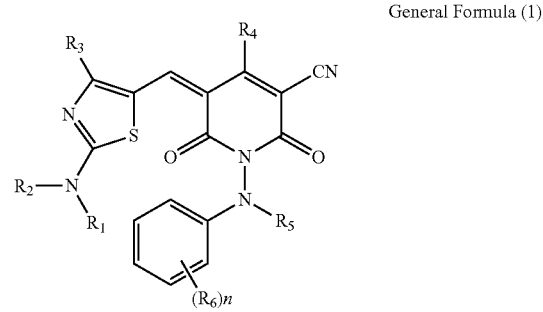

General Formula (1)

In the general formula (1), $R_1$ and $R_2$ each independently represent a substituted or an unsubstituted alkyl group, $R_3$ represents an unsubstituted alkyl group or a substituted or an unsubstituted aryl group, $R_4$ represents an unsubstituted alkyl group, $R_5$ represents a substituted or an unsubstituted alkyl group, a substituted or an unsubstituted aryl group, or a substituted or an unsubstituted acyl group, $R_6$ represents an unsubstituted alkyl group or an alkoxy group, and n represents an integer of 0 to 5, wherein when n is an integer of 2 to 5, a plurality of $R_6$'s may be the same or different from each other.

In addition, the present invention relates to an ink containing the compound described above.

In addition, the present invention relates to a resist composition for a color filter containing the compound described above.

In addition, the present invention relates to a thermal transfer recording sheet containing the compound described above.

In addition, the present invention relates to a toner containing the compound described above.

Further features of the present invention will become apparent from the following description of exemplary embodiments with reference to the attached drawing.

BRIEF DESCRIPTION OF DRAWINGS

The FIGURE is a chart showing a 1H-NMR spectrum of a compound (1-9) of the present invention

DESCRIPTION OF EMBODIMENTS

Hereinafter, although embodiments of the present invention will be described in detail, the present invention is not limited thereto.

Through intensive research carried out by the present inventors to solve the problems described above, it was found that a compound (hereinafter, referred to as "compound of the present invention" in some cases) represented by the following general formula (1) having the structure (N—N-aryl structure) in which an arylamino group is at least bonded to a nitrogen atom of a pyridone ring has a high chroma and also excellent dispersibility even under a high concentration condition.

[Chem. 2]

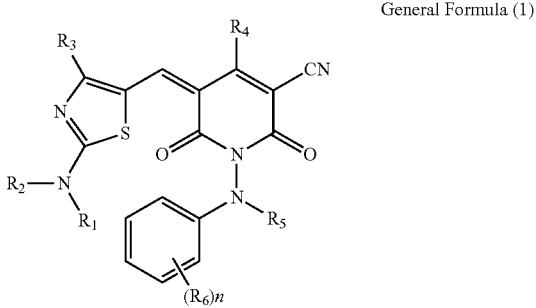

General Formula (1)

In the general formula (1), $R_1$ and $R_2$ each independently represent a substituted or an unsubstituted alkyl group, $R_3$ represents an unsubstituted alkyl group or a substituted or an unsubstituted aryl group, $R_4$ represents an unsubstituted alkyl group, $R_5$ represents a substituted or an unsubstituted alkyl group, a substituted or an unsubstituted aryl group, or a substituted or an unsubstituted acyl group, $R_6$ represents an unsubstituted alkyl group or an alkoxy group, and n represents an integer of 0 to 5, wherein when n is an integer of 2 to 5, a plurality of $R_6$'s may be the same or different from each other.

As disclosed in a related technique, since a compound having the structure (N—N-diacyl structure) in which a diacylamino group is bonded to a nitrogen atom of a pyridone ring has may hydrogen bonding substituents in its molecule, complicated intramolecular and intermolecular interactions may arise. In particular, under a high concentration condition, the aggregation is promoted. On the other hand, in the compound of the present invention, since a sterically twisted structure is formed by a steric structure of the N—N-aryl structure and the pyridone ring, even in a state which is considered to be a high concentration state for a related compound, the intramolecular interaction of the compound or the intermolecular interaction among the compound molecules is suppressed, and hence, it is believed that the aggregation is controlled.

In addition, it was also found that by the use of the compound represented by the general formula (1), even under a condition which is considered to be a high concentration condition for a related compound, an ink, a resist composition for a color filter, a thermal transfer recording sheet, and a toner, each of which has a high chroma and also excellent dispersibility, can be obtained. The above advantage of the present invention is superior to that of a compound having an alkyl amino group (N—N-alkyl structure) in which an alkyl group is bonded to a nitrogen atom of a pyridone ring.

First, the compound represented by the above general formula (1) will be described.

In the general formula (1), although the alkyl group represented by each of $R_1$ and $R_2$ is not particularly limited, a substituted or an unsubstituted alkyl group having 1 to 20 carbon atoms is preferable. In addition, when the above alkyl group is substituted, the number of the carbon atoms thereof includes the number of carbon atoms of the substituent. As the unsubstituted alkyl group, for example, there may be mentioned a linear, a branched, or a cyclic alkyl group, such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, or a 2-ethylhexyl group. In addition, as the substituent of the substituted alkyl group, for example, a cyclohexenyl group may be mentioned. Among those groups mentioned above, in order to improve the chroma and the dispersibility under a high concentration condition, an alkyl group having 1 to 8 carbon atoms is preferable, and a branched alkyl group, such as 2-ethylhexyl group, is more preferable.

In the general formula (1), although the alkyl group represented by $R_3$ is not particularly limited, a linear or a branched alkyl group having 1 to 4 carbon atoms may be mentioned. In particular, there may be mentioned a primary alkyl group, such as a methyl group, an ethyl group, a n-propyl group, or a n-butyl group: a secondary alkyl group, such as an iso-propyl group or a sec-butyl group; or a tertiary alkyl group, such as a tert-butyl group. Among those groups mentioned above, in order to improve the chroma and the dispersibility under a high concentration condition, a tertiary alkyl group, such as a tert-butyl group, is preferable.

In the general formula (1), although the aryl group represented by $R_3$ is not particularly limited, a substituted or an unsubstituted aryl group having 6 to 20 carbon atoms may be mentioned. As the substituent, an alkyl group or an alkoxy group may be mentioned. In addition, when the aryl group is substituted, the number of the carbon atoms thereof includes the number of carbon atoms of the substituent. In addition, the number of substituents may be one or more. As the substituted or the unsubstituted aryl group having 6 to 20 carbon atoms, in particular, there may be mentioned a phenyl group, a 4-methylphenyl group, a 2,4-dimethylphenyl group, a 2,6-dimethylphenyl group, a 3,5-dimethylphenyl group, a 2,4,6-trimethylphenyl group, a pentamethylphenyl group, a 4-methoxyphenyl group, a 2,6-dimethoxyphenyl group, a 2,4-dimethoxyphenyl group, a 3,5-dimethoxyphenyl group, a 2,4,6-trimethoxyphenyl group, or a naphthyl group. Among those groups mentioned above, in order to improve the chroma and the dispersibility under a high concentration condition, a substituted or an unsubstituted phenyl group is preferable, and an unsubstituted phenyl group is more preferable.

In the general formula (1), although the alkyl group represented by $R_4$ is not particularly limited, a linear or a branched alkyl group having 1 to 8 carbon atoms may be mentioned. In particular, for example, there may be mentioned a methyl group, an ethyl group, a n-propyl group, an iso-propyl group, a n-butyl group, an iso-butyl group, a 2-methylbutyl group, a 2,3,3-trimethylbutyl group, or an octyl group. Among those groups mentioned above, in order to improve the chroma and the dispersibility under a high concentration condition, a methyl group, a n-butyl group, a 2-methylbutyl group, or 2,3,3-trimethylbutyl group is preferable.

In the general formula (1), although the alkyl group represented by $R_5$ is not particularly limited, a substituted or an unsubstituted alkyl group having 1 to 20 carbon atoms may be mentioned. In addition, when the alkyl group is substituted, the number of the carbon atoms thereof includes the number of carbon atoms of the substituent. As the unsubstituted alkyl group, for example, there may be mentioned a linear, a branched, or a cyclic alkyl group, such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, a 2-ethylpropyl group, or 2-ethylhexyl group. In addition, as the substituent of the substituted alkyl group, for example, a cyclohexenyl group may be mentioned. Among those groups mentioned above, an alkyl group having 1 to 4 carbon atoms is preferable.

In the general formula (1), although the aryl group represented by $R_5$ is not particularly limited, a substituted or an unsubstituted aryl group having 6 to 10 carbon atoms may be mentioned. As the substituent, an alkyl group or an alkoxy group may be mentioned. In addition, when the aryl group is substituted, the number of the carbon atoms thereof includes the number of carbon atoms of the substituent. In addition, the number of substituents may be one or more. As the substituted or the unsubstituted aryl group having 6 to 10 carbon atoms, for example, there may be mentioned a phenyl group, a 4-methylphenyl group, or 4-methoxyphenyl group.

In the general formula (1), although the acyl group represented by $R_5$ is not particularly limited, a substituted or an unsubstituted acyl group having 1 to 30 carbon atoms may be mentioned. In addition, when the acyl group is substituted, the number of the carbon atoms thereof includes the number of carbon atoms of the substituent. In particular, for example, there may be mentioned a formyl group; a substituted or an unsubstituted alkyl carbonyl group having 2 to 30 carbon atoms, such as an acetyl group, a propionyl group, or a pivaloyl group; a substituted or an unsubstituted aryl carbonyl group having 7 to 30 carbon atoms, such as a benzoyl group or a naphthoyl group; or a heterocyclic carbonyl group, such as 2-pyridyl carbonyl group or a 2-fury) carbonyl group. Among those groups mentioned above, in order to improve the chroma and the dispersibility under a high concentration condition, an acetyl group, a pivaloyl group, or benzoyl group is preferable, and an acetyl group or a benzoyl group is more preferable.

In the general formula (1), $R_6$ represents an alkyl group or an alkoxy group. In addition, when n is an integer of 2 to 5, a plurality of $R_6$'s may be the same or different from each other.

Although the alkyl group represented by $R_6$ is not particularly limited, an unsubstituted alkyl group having 1 to 20 carbon atoms may be mentioned. In particular, as the unsubstituted alkyl group, for example, there may be mentioned a linear, a branched, or a cyclic alkyl group, such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl group, or 2-ethylhexyl group. Among those groups mentioned above, an alkyl group having 1 to 4 carbon atoms is preferable.

In the general formula (1), although the alkoxy group represented by $R_6$ is not particularly limited, a linear or a branched alkoxy group having 1 to 4 carbon atoms may be mentioned. In particular, for example, there may be mentioned a methoxy group, an ethoxy group, a propoxy group, or a butoxy group.

In the general formula (1), n represents an integer of 0 to 5. As described above, when n is an integer of 2 to 5, a plurality of $R_6$'s may be the same or different from each other. In order to improve the chroma and the dispersibility under a high concentration condition, n is preferably 0 or 1, and 0 is more preferable.

Next, a manufacturing method of the compound represented by the general formula (1) according to the present invention will be described. The compound of the present invention may be synthesized with reference to a known method described in PTL 3. Hereinafter, although one example of the manufacturing method of the compound of the present invention will be described, the manufacturing method is not limited thereto.

[Chem.3]

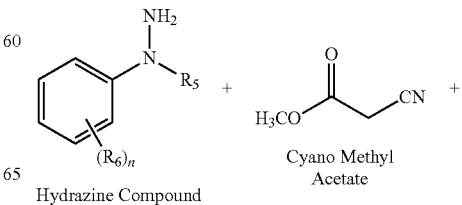

Hydrazine Compound     Cyano Methyl Acetate

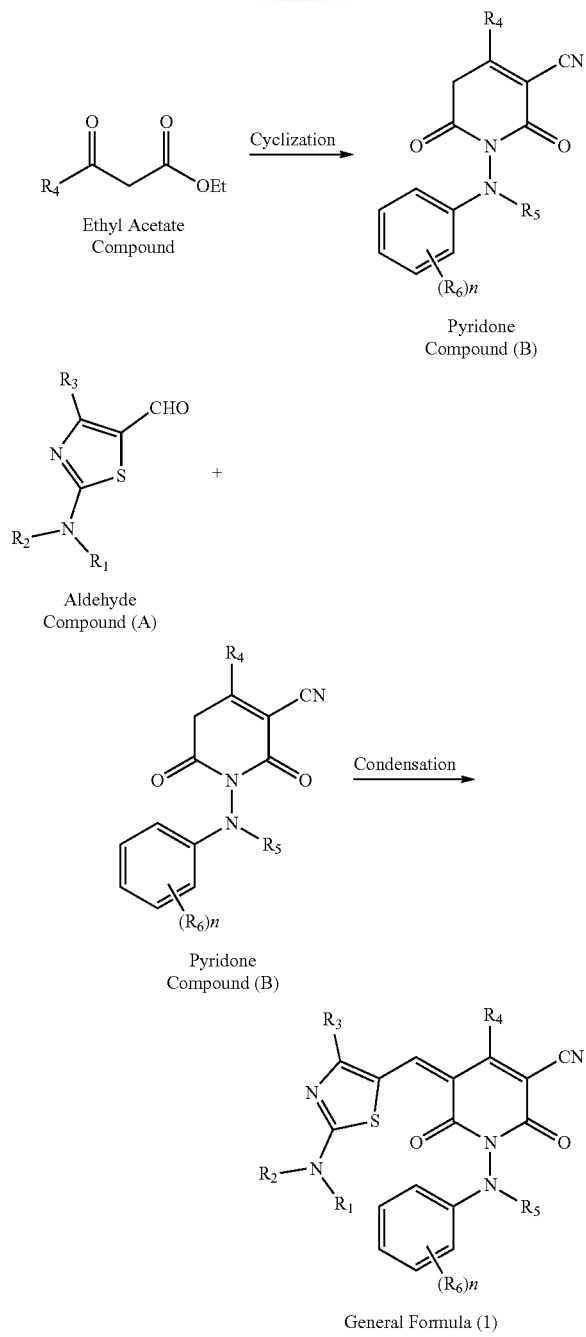

Cyclization Step

The pyridone compound (B) can be synthesized by a cyclization reaction in which three components, which are the hydrazine compound, cyano methyl acetate, and the ethyl acetate compound, are coupled to each other. Although the cyclization reaction may be performed without using a solvent, the reaction is preferably performed in the presence of a solvent. As the solvent, any solvents may be used as long as the cyclization reaction is not inhibited, and for example, water, methanol, ethanol, acetic acid, or toluene may be mentioned. Those solvents may be used alone, or at least two types thereof may be used in combination. A mixing ratio when at least two types of solvents are used in combination may be arbitrarily determined. The use amount of the above solvent is with respect to cyano methyl acetate, preferably 0.1 to 1,000 percent by mass and more preferably 1.0 to 150 percent by mass.

In addition, in this cyclization reaction, in order to promote the reaction, a base is preferably used. Although the base is not particularly limited, for example, there may be mentioned an organic base, such as pyridine, 2-methylpyridine, piperidine, diethylamine, diisopropylamine, triethylamine, phenylethylamine, isopropylethylamine, methylaniline, 1,4-diazabicyclo[2.2.2]octane (DABCO), tetrabutylammonium hydroxide, or 1,8-diazabicyclo[5.4.0]undecene (DBU); an organic metal, such as n-butyl lithium or tort-butyl magnesium chloride; an inorganic base, such as sodium boron hydride, metal sodium, potassium hydride, or calcium oxide; or a metal alkoxide, such as potassium tert-butoxide, sodium tert-butoxide, or sodium ethoxide. Among those bases mentioned above, triethylamine or piperidine is preferable, and triethylamine is more preferable. The use amount of the above base is with respect to cyano methyl acetate, preferably 0.01 to 100 percent by mass, more preferably 0.1 to 20 percent by mass, and particularly preferably 0.5 to 5 percent by mass. In addition, as is the above base, a weakly basic salt, such as potassium acetate, may also be used.

After the cyclization reaction is completed, if needed, by performing purification, such as distillation, recrystallization, or silica-gel chromatography, a preferable pyridone compound (B) can be obtained. As the preferable pyridone compound (B), although compounds (B-1) to (B-12) are show below, the present invention is not limited thereto.

[Chem.4]

(B-1)

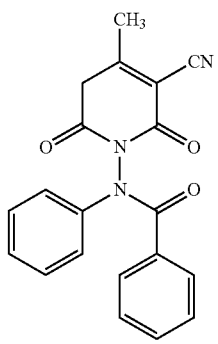

In addition, $R_1$ to $R_6$ and n of the compounds in the above reaction formulas are the same as those described above. In addition, although the compound represented by the general formula (1) includes cis-trans isomers, the isomers are both in the range of the present invention, and the compound represented by the general formula (1) may also be a mixture thereof.

As described above, the compound of the present invention represented by the general formula (1) can be synthesized by a condensation reaction between the aldehyde compound (A) and the pyridone compound (B). First, a cyclization step to obtain the pyridone compound (B) will be described.

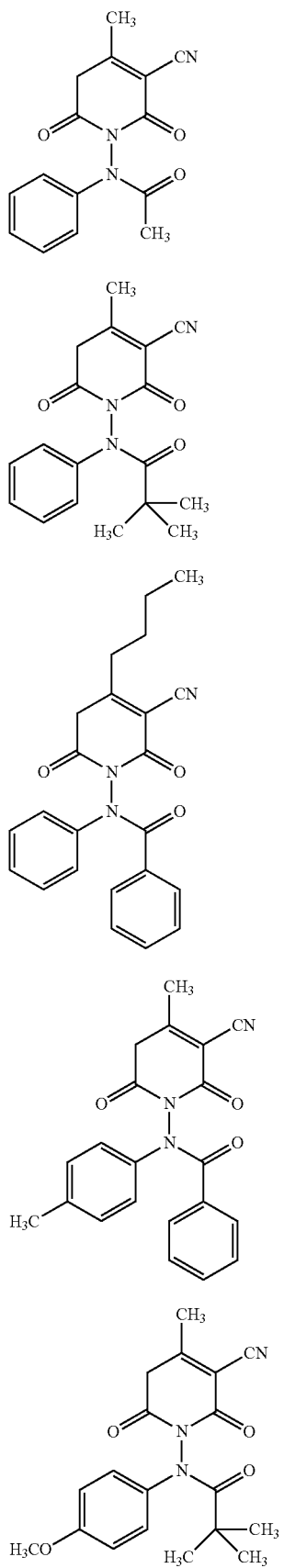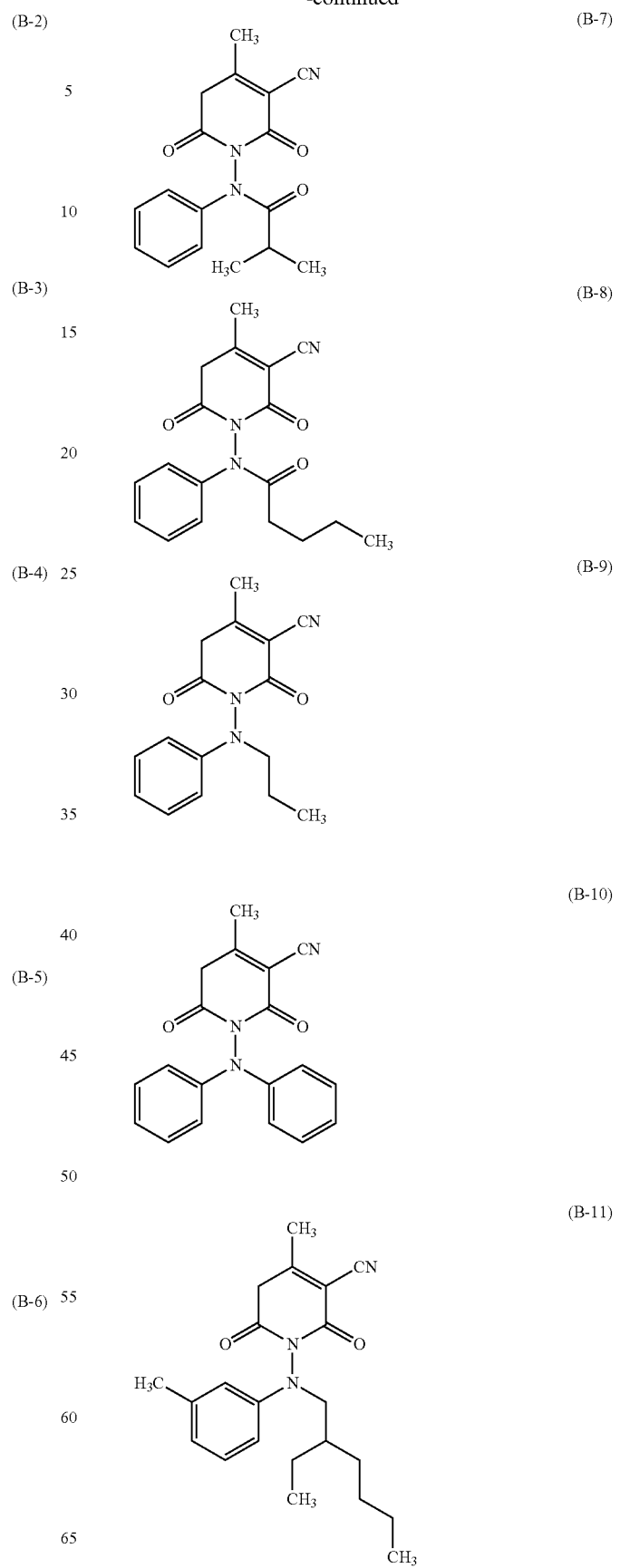

-continued (B-12)
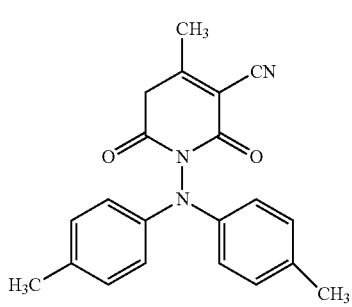

Condensation Step

Next, a condensation step to obtain the compound of the present invention represented by the general formula (1) will be described. The compound of the present invention can be synthesized by a condensation reaction between the aldehyde compound (A) and the pyridone compound (B). The aldehyde compound (A) can be synthesized with reference to a known method disclosed in PTL 3. As a preferable aldehyde compound (A), although compounds (A-1) to (A-12) are shown below, the present invention is not limited thereto.

[Chem.5]

(A-1)
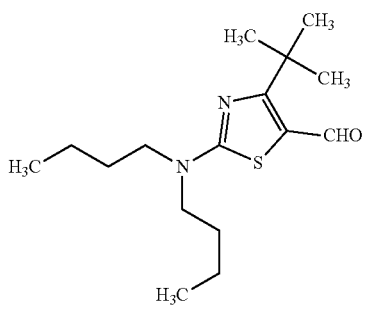

(A-2)
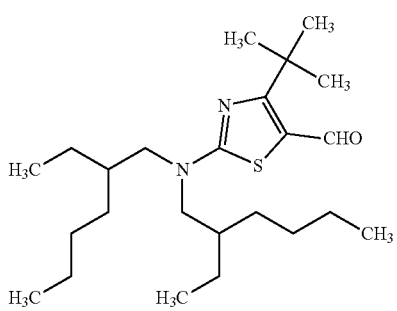

(A-3)
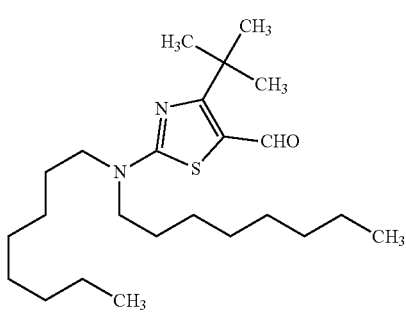

(A-4)
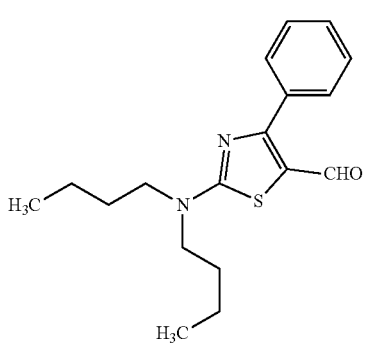

(A-5)
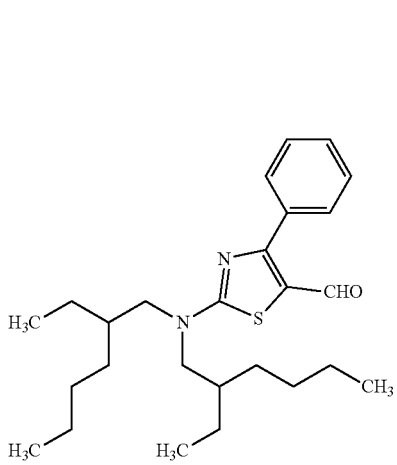

(A-6)
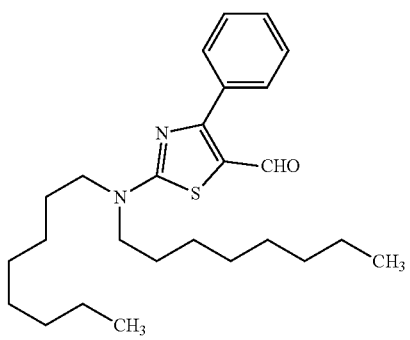

(A-7)
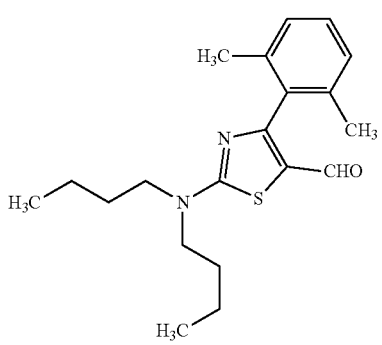

(A-8)

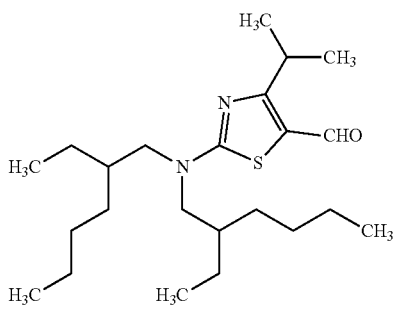

(A-9)

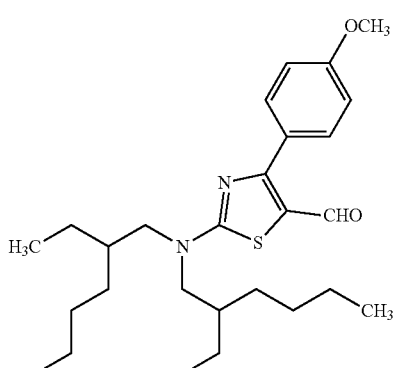

(A-10)

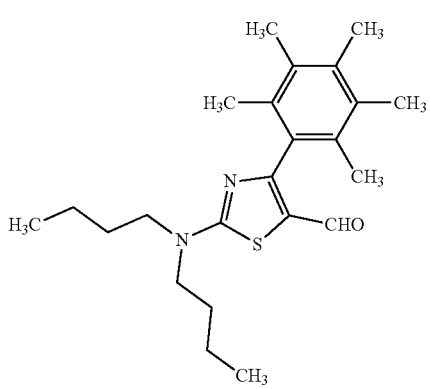

(A-11)

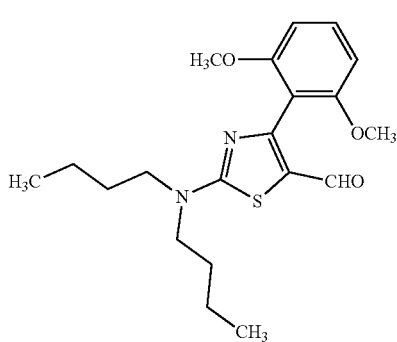

(A-12)

Although this condensation reaction may be performed without using a solvent, the reaction is preferably performed in the presence of a solvent. As the solvent, any solvents may be used as long as the reaction is not inhibited, and for example, there may be mentioned chloroform, dichloromethane, N,N-dimethylformamide, toluene, xylene, tetrahydrofuran, dioxane, acetonitrile, ethyl acetate, methanol, ethanol, or isopropyl alcohol. Those solvents may be used alone, or at least two types thereof may be used in combination. A mixing rate when at least two types thereof are used in combination may be arbitrarily determined. The use amount of the above reaction solvent is with respect to the aldehyde compound (A), preferably 0.1 to 1,000 percent by mass and more preferably 1.0 to 150 percent by mass.

The reaction temperature of this condensation reaction is preferably in a range of −80° C. to 250° C. and more preferably in a range of −20° C. to 150° C. In general, this condensation reaction is completed within 24 hours.

In addition, in this condensation reaction, in order to promote the reaction, an acid or a base is preferably used. As the acid, for example, there may be mentioned an inorganic acid, such as hydrochloric acid, sulfuric acid, or phosphoric acid; or an organic acid, such as p-toluene sulfonic acid, formic acid, acetic acid, propionic acid, or trifluoroacetic acid. In addition, as is the acid described above, a weakly acidic salt, such as ammonium formate or ammonium acetate, may also be used. Among those acids mentioned above, p-toluene sulfonic acid, ammonium formate, or ammonium acetate is preferable. The use amount of the acid mentioned above is with respect to the aldehyde compound (A), preferably 0.01 to 20 percent by mass and more preferably 0.1 to 5 percent by mass.

In addition, as the base, for example, there may be mentioned an organic base, such as pyridine, 2-methylpyridine, piperidine, diethylamine, diisopropylamine, triethylamine, phenylethylamine, isopropylethylamine, methylaniline, 1,4-diazabicyclo[2.2.2]octane (DABCO), or tetrabutylammonium hydroxide, 1,8-diazabicyclo[5.4.0]undecene (DBU); an organic metal, such as n-butyl lithium or tert-butyl magnesium chloride; an inorganic base, such as sodium boron hydride, metal sodium, potassium hydride, or calcium oxide; or a metal alkoxide, such as potassium tert-butoxide, sodium tert-butoxide, or sodium ethoxide. Among those bases mentioned above, triethylamine or piperidine is preferable, and triethylamine is more preferable. The use amount of the above base is with respect to the aldehyde compound (A), preferably 0.1 to 20 percent by mass and more preferably 0.2 to 5 percent by mass. In addition, as is the above base, a weakly basic salt, such as potassium acetate, may also be used.

After the condensation reaction is completed, a post-treatment is performed in accordance with a post-treatment method which is generally performed in an organic synthesis reaction, and if needed, purification, such as a liquid separation operation, recrystallization, reprecipitation, or column chromatography, is performed, so that the compound of the present invention represented by the general formula (1) can be obtained at a high purity.

Although the following compounds (1-1) to (1-19) are each shown as a preferable compound of the present invention represented by the general formula (1), the present invention is not limited thereto.

[Chem. 6]
(1-1) 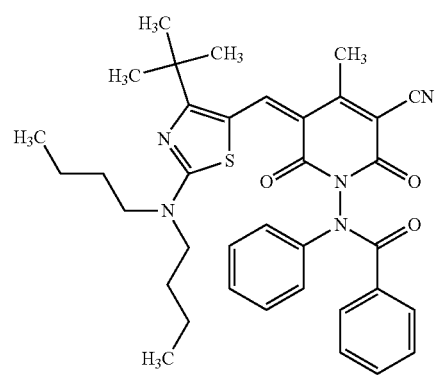
(1-2) 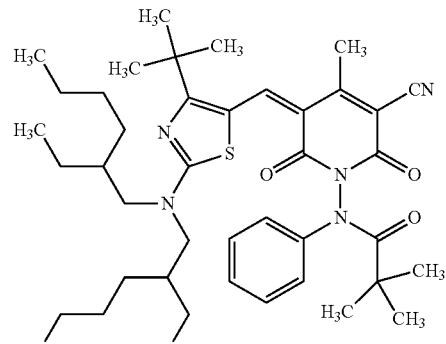
(1-3) 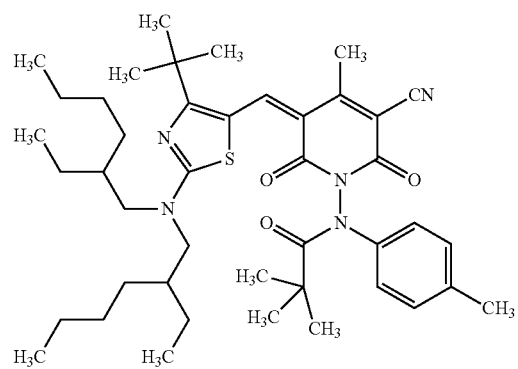
(1-4) 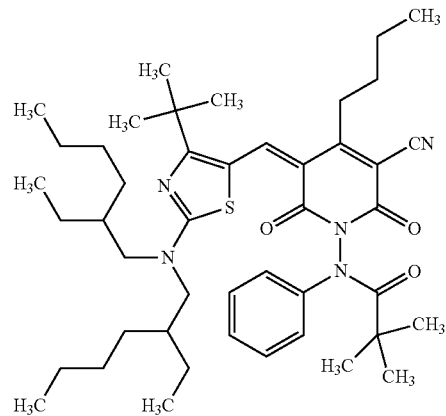
(1-5) 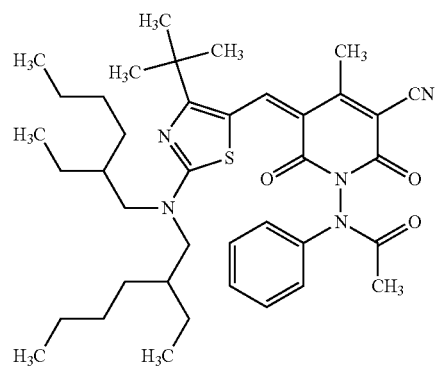
(1-6) 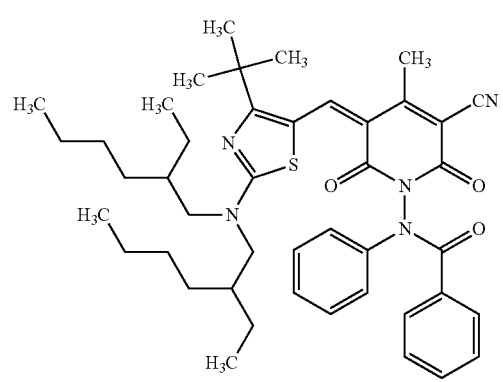
(1-7) 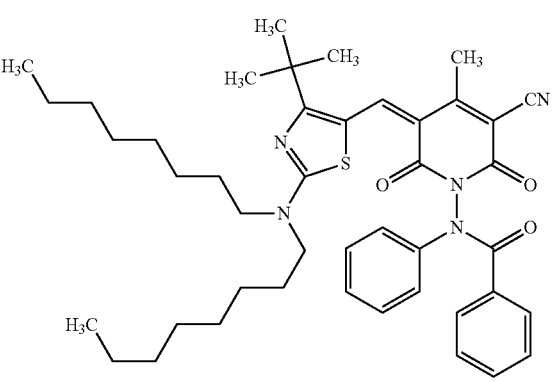
(1-8) 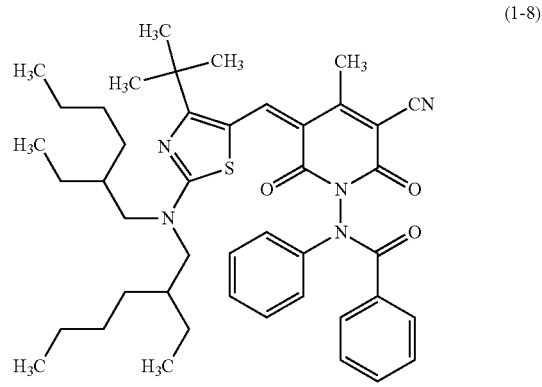

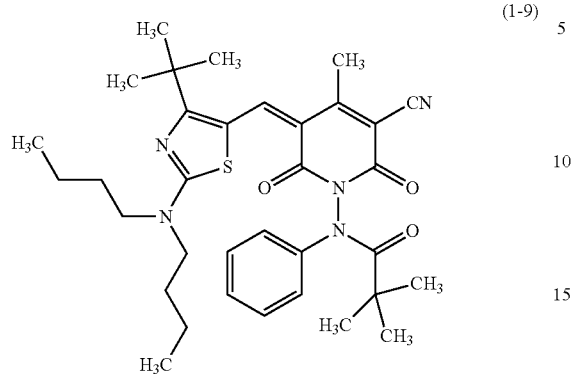
(1-9)
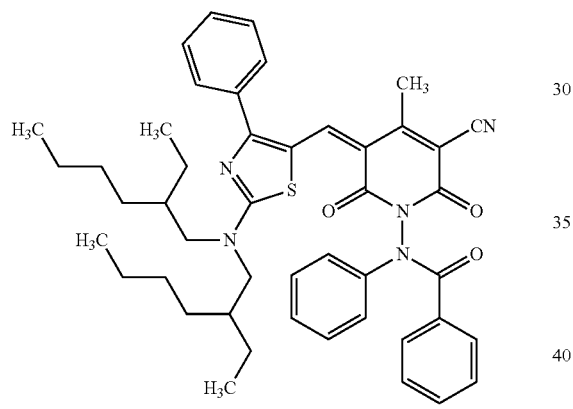
(1-10)
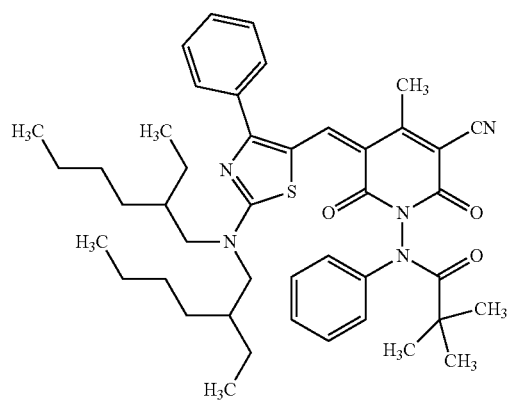
(1-11)
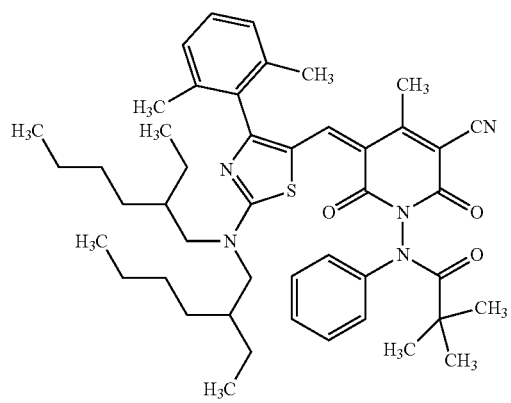
(1-12)
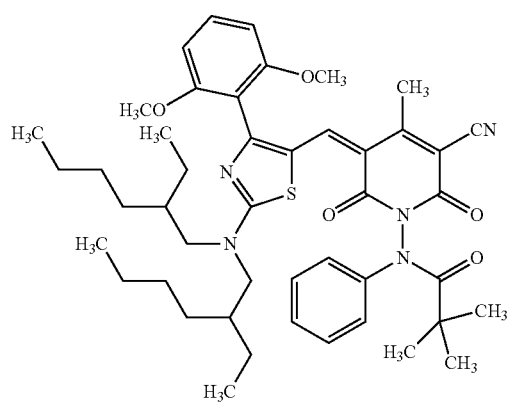
(1-13)
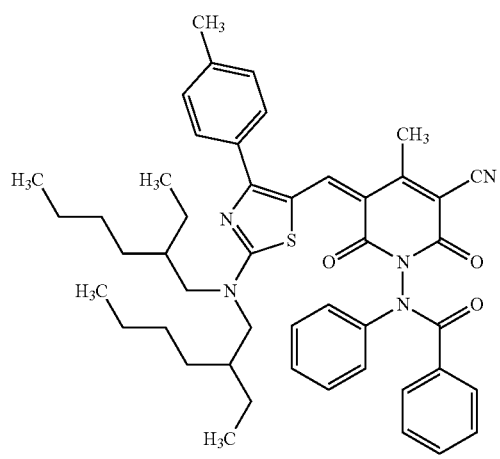
(1-14)

(1-15)
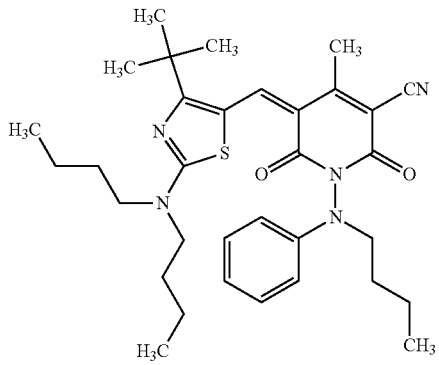

(1-16)
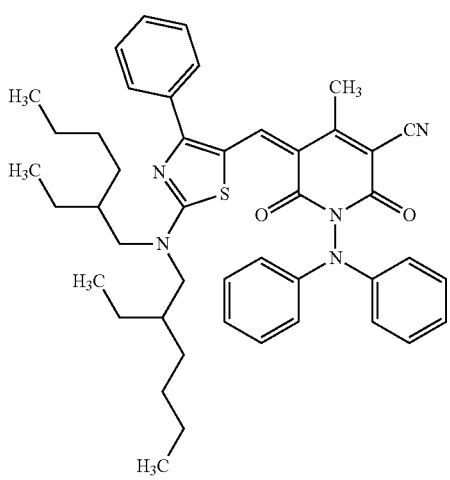

(1-17)
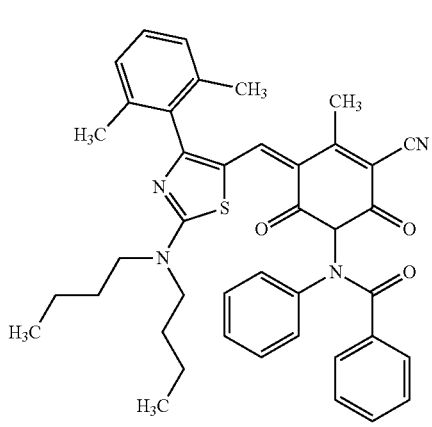

(1-18)
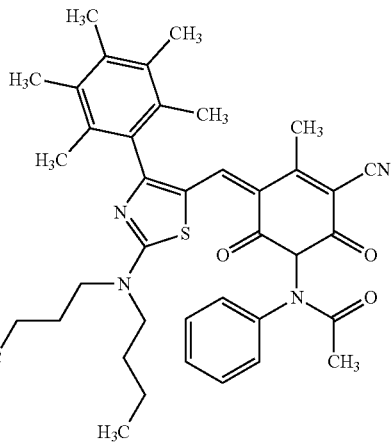

(1-19)
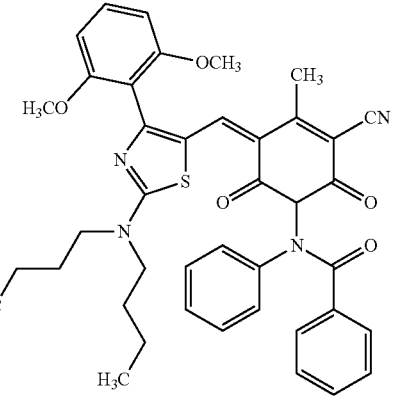

The compounds represented by the above general formula (1) may be used alone, or in order to adjust the color tone and the like in accordance with the application, at least two types thereof may be used in combination. Furthermore, the above compounds each may also be used in combination with a known pigment and/or dye. The number of the known pigments and/or dyes to be used in combination may be two or more.

Hereinafter, an ink, a resist composition for a color filter, a thermal transfer recording sheet, and a toner, each of which uses the compound represented by the above general formula (1), will be described in this order.

Ink

First, an ink according to the present invention will be described. Since having a high chroma and also excellent dispersibility even under a high concentration condition, the compound represented by the general formula (1) is also preferably used as a colorant of ink. The ink of the present invention includes a medium and the compound represented by the general formula (1) as a colorant. In the ink of the present invention, a constituent component other than the compound represented by the above general formula (1) is appropriately selected in accordance with the application of ink. In addition, as long as the characteristics for various types of applications are not degraded, for example, at least one additive may also be appropriately added.

The ink of the present invention is preferably used, besides as an ink jet ink, also as a printing ink, a paint, a writing ink, a textile printing ink, or a digital textile ink.

When the ink of the present invention is used as a textile printing ink, although cloth on which textile printing can be performed is not particularly limited, cloth formed of fibers containing a polyester, an acetate, or a triacetate may be mentioned by way of example. The cloth may be in the form of woven fabric, knitted fabric, nonwoven fabric, or the like. In addition, there may also be used cloth formed of fibers of a cotton, a silk, a hemp, a polyurethane, an acrylic resin, a nylon, a sheep wool, or a rayon and cloth formed of at least two types of fibers mentioned above in combination.

The diameter of yarns which form the cloth is preferably in a range of 10 to 100 deniers. In addition, although the diameter of fibers which form the yarn is not particularly limited, the diameter thereof is preferably one denier or less.

The ink of the present invention can be prepared as described below.

The compound of the present invention is gradually added to a medium with stirring together with, if needed, another colorant, an emulsifier, a resin, and the like so as to be sufficiently compatible with the medium. Furthermore, a stable dissolution state or a fine dispersion state is formed by applying a mechanical shearing force using a dispersing machine, so that the ink of the present invention can be obtained.

Medium 1

In the present invention, the "medium" indicates water or an organic solvent. When an organic solvent is used as the medium, the type of organic solvent is to be selected in accordance with the purpose or the application of ink and is not particularly limited. As the organic solvent, for example, there may be mentioned an alcohol, such as methanol, ethanol, a modified ethanol, isopropyl alcohol, n-butanol, isobutanol, butanol, sec-butanol, 2-methyl-2-butanol, 3-pentanol, octanol, benzyl alcohol, or cyclohexanol; a glycol, such as methyl cellosolve, ethyl cellosolve, diethylene glycol, or diethylene glycol monobutyl ether; a ketone, such as acetone, methyl ethyl ketone, or methyl isobutyl ketone; an ester, such as ethyl acetate, butyl acetate, ethyl propionate, or cellosolve acetate; an aliphatic hydrocarbon, such as hexane, octane, petroleum ether, or cyclohexane; an aromatic hydrocarbon, such as benzene, toluene, or xylene; a halogenated hydrocarbon, such as carbon tetrachloride, trichloroethylene, or tetrabromoethane; an ether, such as diethyl ether, dimethyl glycol, trioxane, or tetrahydrofuran; an acetal, such as methyl or diethyl acetal; an organic acid, such as formic acid, acetic acid, or propionic acid; or a sulfur- or a nitrogen-containing organic compound, such as nitrobenzene, dimethylamine, monoethanolamine, pyridine, dimethyl sulfoxide, or dimethylformamide.

In addition, as the organic solvent, a polymerizable monomer may also be used. As the polymerizable monomer, an addition polymerizable monomer or a condensation polymerizable monomer may be mentioned, and an addition polymerizable monomer is preferable. As the polymerizable monomer, for example, there may be mentioned a styrene-based monomer, such as styrene, α-methylstyrene, α-ethylstyrene, α-methylstyrene, m-methylstyrene, p-methylstyrene, o-ethylstyrene, m-ethylstyrene, or p-ethylstyrene; an acrylate monomer, such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, or amide acrylate; an methacrylate monomer, such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, or amide methacrylate; an olefinic monomer, such as ethylene, propylene, butylene, butadiene, isoprene, isobutylene, or cyclohexane; a halogenated vinyl monomer, such as vinyl chloride, vinylidene chloride, vinyl bromide, or vinyl iodide; a vinyl ester monomer, such as vinyl acetate, vinyl propionate, or vinyl benzoic acid; a vinyl ether monomer, such as vinyl methyl ether, vinyl ethyl ether, or vinyl isobutyl ether; or a vinyl ketone monomer, such as vinyl methyl ketone, vinyl hexyl ketone, or methyl isopropenyl ketone. Those monomers may be used alone, or if needed, at least two types thereof may be used in combination.

Colorant 1

As the colorant which forms the ink of the present invention, although the compound represented by the general formula (1) is used, the compound may be used alone, or at least two types thereof may be used in combination. In addition, as long as the solubility or the dispersibility of the compound to the medium is not degraded, at least one another colorant, such as a known dye, may also be used together. Although the another colorant to be used together is not particularly limited, for example, a condensed azo compound, an azo metal complex, or a methine compound may be mentioned.

The content of the above colorant is with respect to 1,000 parts by mass of the medium, preferably 1.0 to 30 parts by mass, more preferably 2.0 to 20 parts by mass, and particularly preferably 3.0 to 15 parts by mass. When the content is in the range described above, a sufficient coloring power can be obtained, and the dispersibility of the colorant is improved.

Emulsifier

When water is used as the medium of the ink according to the present invention, in order to obtain a preferable dispersion stability of the colorant, if needed, an emulsifier may also be added. Although the emulsifier is not particularly limited, a cationic surfactant, an anionic surfactant, or a nonionic surfactant may be mentioned.

As the cationic surfactant, for example, there may be mentioned dodecylammonium chloride, dodecylammonium bromide, dodecyltrimethylammonium bromide, dodecylpyridinium chloride, dodecylpyridinium bromide, or hexadecyltrimethylammonium bromide.

As the above anionic surfactant, for example, there may be mentioned a fatty acid soap, such as sodium stearate or sodium dodecanoate, sodium dodecyl sulfate, sodium dodecylbenzene sulfate, or sodium lauryl sulfate.

As the nonionic surfactant, for example, there may be mentioned dodecyl polyoxyethylene ether, hexadecyl polyoxyethylene ether, nonylphenyl polyoxyethylene ether, lauryl polyoxyethylene ether, sorbitan monooleate polyoxyethylene ether, or monodecanoyl sucrose.

Resin

The ink of the present invention may further contain a resin. The type of resin is to be determined in accordance with the purpose and the application of ink and is not particularly limited. For example, there may be mentioned a styrene-based polymer, an acrylic acid-based polymer, a methacrylic acid-based polymer, a polyester resin, a poly(vinyl ether) resin, a poly(vinyl methyl ether) resin, a poly(vinyl alcohol) resin, a poly(vinyl butyral) resin, a polyurethane resin, or a polypeptide resin. Those resins may be used alone, or if needed, at least two types thereof may be used in combination.

Although the dispersing machine is not particularly limited, for example, a medium type dispersing machine, such as a rotating shear type homogenizer, a ball mill, a sand mill, or an attritor, or a high-pressure counter collision type dispersing machine may be used.

As described above, since including the compound represented by the general formula (1), the ink of the present invention has a high chroma and also excellent dispersibility even under a high concentration condition.

Resist Composition for Color Filter and Color Filter

Next, a resist composition for a color filter (hereinafter, referred to as "resist composition of the present invention" in some cases) of the present invention will be described. Since having a high chroma and also excellent dispersibility even under a high concentration condition, the compound represented by the general formula (1) is preferably used to adjust the color tone of a resist composition for a color filter. In addition, by the use of the resist composition of the present invention, a color filter having a high chroma and also excellent dispersibility even under a high concentration condition can be obtained.

The resist composition of the present invention includes a binder resin, a medium, and the compound of the present invention as a colorant. The resist composition of the present invention can be obtained as described below. The compound of the present invention and the binder resin are added to the medium with stirring. In this step, if needed, a polymerizable monomer, a polymerization initiator, a photo acid generator, and the like may also be added. Subsequently, since a mechanical shearing force is applied using a dispersing machine, the materials described above are stably dissolved or finely dispersed in the medium, so that the resist composition of the present invention can be obtained.

Binder Resin 1

As a binder resin usable for the resist composition of the present invention, any resin may be used as long as a light irradiation portion or a light shielding portion formed therefrom in an exposure step of pixel formation can be dissolved by an organic solvent, an alkali aqueous solution, water, or a commercially available developer liquid. Among those mentioned above, in view of workability and easy treatment performed after the resist formation, a binder resin having a composition which can be developed by water or an alkali aqueous solution is preferable.

As the binder resin described above, there may be used a binder resin obtained by copolymerization performed in accordance with a known method at an appropriate mixing ratio between a hydrophilic polymerizable monomer, such as acrylic acid, methacrylic acid, N-2-hydroxyethyl)acrylamide, N-vinyl pyrrolidone, or a polymerizable monomer having an ammonium salt, and a lipophilic polymerizable monomer, such as an acrylic acid ester, a methacrylic acid ester, vinyl acetate, styrene, or N-vinyl carbazole. The binder resin as described above may be used in combination with a radical polymerizable monomer having an ethylenic unsaturated group, a cationic polymerizable monomer having an oxirane ring or an oxetane group, a radical generator, an acid generator, and a base generator. This type of binder resin may be used as a negative type resist composition in which the solubility of a material at an exposure portion to a developer liquid is decreased by exposure, and a light shielding portion is only removed by development.

In addition, a resin having a quinone diazide group which is cleaved by light to generate a carboxylic acid, a resin having a group which is cleaved by an acid, such as a tetrahydropyranyl ether or a tert-butyl carbonate ester of a polyhydroxystyrene, and an acid generator which generates an acid by exposure may be used in combination. This type of resin may be used as a positive type resist composition in which the solubility of a material at an exposure portion to a developer liquid is improved by exposure, and the exposure portion is only removed by development.

When the resist composition of the present invention is the above negative type resist composition, as the binder resin, a polymerizable monomer (hereinafter, referred to as "photopolymerizable monomer" in some cases) which performs addition polymerization by exposure is preferably used. As the photopolymerizable monomer, a compound having at least one addition-polymerizable ethylenic unsaturated double bond in its molecule and a melting point of 100° C. or more at normal pressure is preferably used. In particular, for example, there may be mentioned a monofunctional acrylate or methacrylate, such as a polyethylene glycol monoacrylate, a polyethylene glycol monomethacrylate, a polypropylene glycol monoacrylate, a polypropylene glycol monomethacrylate, phenoxyethyl acrylate, or phenoxyethyl methacrylate; a polyfunctional acrylate or methacrylate, such as a polyethylene glycol diacrylate, a polyethylene glycol dimethacrylate, a polypropylene glycol diacrylate, a polypropylene glycol dimethacrylate, trimethylolethane triacrylate, trimethylolethane trimethacrylate, trimethylolpropane triacrylate, trimethylolpropane trimethacrylate, trimethylolpropane diacrylate, trimethylolpropane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylolpropane tri(acryloyloxypropyl) ether, tri(acryloyloxyethyl)isocyanurate, tri(acryloyloxyethyl)cyanurate, glycerin triacrylate, or glycerin trimethacrylate; or a polyfunctional acrylate or methacrylate which is obtained in such a way that after an ethylene oxide or a propylene oxide is added to a polyfunctional alcohol, such as trimethylol propane or glycerin, the adduct thus obtained is acrylated or methacrylated, Furthermore, there may also be used a urethane acrylate, a polyester acrylate, or a polyfunctional epoxy acrylate or epoxy methacrylate which is a reaction product between an epoxy resin and acrylic acid or methacrylic acid.

Among the above photopolymerizable monomers, trimethylolpropane triacrylate, trimethylolpropane trimethacrylate, pentaerythritol tetraacrylate, pentaerythritol tetramethacrylate, dipentaerythritol hexaacrylate, dipentaerythritol hexamethacrylate, dipentaerythritol pentaacrylate, or dipentaerythritol pentamethacrylate is preferably used. The above photopolymerizable monomers may be used alone, or if needed, at least two types thereof may be used in combination.

The content of the above photopolymerizable monomer is with respect to the mass (total solid component) of the resist composition according to the present invention, preferably 5 to 50 percent by mass and more preferably 10 to 40 percent by mass. When the content is 5 to 50 percent by mass, the sensitivity to exposure can be further improved, and an adhesion property of the resist composition is also improved.

When the resist composition of the present invention is the above negative type resist composition, a photopolymerization initiator may also be added. As the photopolymerization initiator, a vicinal poly-keto aldol compound, an α-carbonyl compound, an acyloin ether, a multibranched quinone compound, a combination between a triallyl imidazole dimer and p-aminophenyl ketone, or a tri-oxadiazole compound may be mentioned. Among those mentioned above, 2-benzyl-2-dimethylamino-1-(4-morpholinophenyl)

butanone (trade name: Irgacure 369, manufactured by BASF) is preferable. Incidentally, upon the formation of pixels using the resist composition of the present invention, when electron rays are used, the above photopolymerization initiator is not essential.

In addition, when the resist composition of the present invention is the positive type resist composition described above, if needed, a photo acid generator may also be added. As the photo acid generator, a known photo acid generator may be used, and for example, a salt of an anion and an onium ion, such as a sulfonium, an iodonium, a selenium, an ammonium, or a phosphonium ion, may be used.

As the sulfonium ion mentioned above, for example, there may be mentioned triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, or phenacyltetrahydrothiophenium.

As the iodonium ion mentioned above, for example, there may be mentioned diphenyliodonium, di-p-tolyliodonium, bis(4-dodecylphenyl)iodonium, bis(4-methoxyphenyl)iodonium, or (4-octyloxyphenyl)phenyliodonium.

As the selenium ion mentioned above, for example, there may be mentioned triphenylselenium, tri-p-tolylselenium, tri-o-tolylselenium, tris(4-methoxyphenyl)selenium, 1-naphthyldiphenylselenium, tris(4-fluorophenyl)selenium, tri-1-naphtylselenium, or tri-2-naphtylselenium.

As the ammonium ion mentioned above, for example, there may be mentioned a tetraalkylammonium, such as tetramethylammonium, ethyltrimethylammonium, di-ethyldimethylammonium, triethylmethylammonium, tetraethylammonium, trimethyl-n-propylammonium, trimethylisopropylammonium, trimethyl-n-butylammonium, or trimethylisobutylammonium.

As the phosphonium ion mentioned above, for example, there may be mentioned tetraphenylphosphsphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, or tetraethylphosphonium.

As the anion mentioned above, for example, there may be mentioned a perhalogen acid ion, such as $ClO_4^-$ or $BrO_4^-$; a halogenated sulfonic acid ion, such as $FSO_3^-$ or $ClSO_3^-$; a sulfuric acid ion, such as $CH_3SO_4^-$, $CF_3SO_4^-$, or $HSO_4^-$; a carbonic acid ion, such as $HCO_3^-$ or $CH_3CO_3^-$; an aluminic acid ion, such as $AlCl_4^-$ or $AlF_4^-$; a hexafluoro-bismuthic acid ion; a carboxylic acid ion, such as $CH_3COO^-$, $CF_3COO^-$, $C_6H_5COO^-$, $CH_3C_6H_4COO^-$, $C_6F_5COO^-$, or $CF_3C_6H_4COO^-$; or aryl boric acid ion, such as $B(C_6H_5)_4^-$ or $CH_3CH_2CH_2CH_2B(C_6H_5)_3^-$; a thiocyanate ion, or a nitric acid ion; however, the anion is not limited thereto.

Medium 2

In the resist composition of the present invention, as the medium to dissolve or disperse the compound of the present invention and the binder resin together with the photopolymerizable monomer, the photopolymerization initiator, and the photo acid generator, each of which is added if needed, water or an organic solvent may be used. As the organic solvent, for example, there may be mentioned cyclohexanone, ethyl cellosolve acetate, butyl cellosolve acetate, 1-methoxy-2-propyl acetate, diethylene glycol dimethyl ether, ethylbenzene, 1,2,4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropyl alcohol, butanol, methyl isobutyl ketone, or a petroleum solvent. Those organic solvents may be used alone, or at least two types thereof may be used in combination.

Colorant 2

As the colorant which forms the resist composition of the present invention, although the compound represented by the general formula (1) may be used alone, at least two types thereof may also be used in combination. In addition, in order to obtain desired spectral characteristics, another dye may also be used together for color tone adjustment. Although the dye which may be used together is not particularly limited, a condensed azo compound, an azo metal complex, a diketo pyrrolo pyrrole compound, an anthraquinone compound, a quinacridone compound, an naphthol compound, a benzimidazolon compound, a thioindigo compound, a perylene compound, a methine compound, an allylamide compound, and a base dye lake compound may be mentioned.

To the resist composition of the present invention, besides the additives described above, if needed, a UV absorber and a silane coupling agent which is used to improve the adhesion to a glass substrate in filter formation may also be added.

Although the dispersing machine is not particularly limited, for example, a medium type dispersing machine, such as a rotating shear type homogenizer, a ball mill, a sand mill, or an attritor, or a high-pressure counter collision type dispersing machine may be used.

As described above, since the resist composition of the present invention includes the compound represented by the general formula (1), even under a high concentration condition, the chroma is high, and the dispersibility of the compound is also excellent. In addition, in a color filter in which at least two types of pixels having different spectral characteristics are arranged adjacent to each other, when the resist composition of the present invention is used for a pixel which forms at least one of a plurality of pixel colors (such as red, green, and blue), a color filter having a high chroma can be obtained.

Thermal Transfer Recording Sheet

Next, a thermal transfer recording sheet of the present invention will be described. Since having a high chroma and also excellent dispersibility even under a high concentration condition, the compound of the present invention can be preferably used for a thermal transfer recording sheet.

The thermal transfer recording sheet according to the present invention includes a substrate and a coloring material layer formed thereon using a composition containing the compound of the present invention. The coloring material layer includes at least a yellow layer, a magenta layer, and a cyan layer.

In a thermal transfer recording method, in a state in which the coloring material layer of the thermal transfer recording sheet is overlapped with an image receiving sheet on which a coloring material receiving layer is provided, when the thermal transfer recording sheet is heated using a heating unit such as a thermal head, coloring materials in the sheet are transferred to the image receiving sheet, so that image formation is performed.

The above coloring material layer includes a coloring material containing the compound represented by the general formula (1), a binder resin, and a medium together with, if needed, a surfactant and a wax. A method for forming the thermal transfer recording sheet of the present invention is not particularly limited, and in general, the thermal transfer recording sheet is obtained as described below.

The coloring material containing the compound represented by the general formula (1) and the binder resin are gradually added with stirring to the medium together with, if needed, the surfactant and the wax so as to enable the materials to be sufficiently compatible to each other. Subsequently, by applying a mechanical shearing force using a dispersing machine, the above composition is stably dissolved or is dispersed into fine particles, so that a dispersion liquid (ink) is prepared. This dispersion liquid is applied to a base film functioning as a substrate and is then dried, so that the coloring material layer is formed. Furthermore, if needed, for example, a transfer protective layer and a heat resistant lubricant layer, which will be described later, are formed, so that the thermal transfer recording sheet of the present invention can be obtained. In addition, the thermal transfer recording sheet of the present invention is not limited to the thermal transfer recording sheet formed by the manufacturing method described above. Hereinafter, the components used for the coloring material layer will be described in detail.

Coloring Material

Although the compound represented by the general formula (1) is used as the coloring material, the above compound may be used alone, or at least two types thereof may be used in combination. In addition, a coloring material which has been used in the past for thermal transfer may also be used together. As for the coloring material to be used together, the hue, the printing sensitivity, the light resistance, the storage stability, the solubility to the binder resin, and the like thereof are required to be taken into consideration. The use amount of the coloring material is with respect to 100 parts by mass of the binder resin contained in the coloring material layer, 1 to 150 parts by mass and is preferably 50 to 120 parts by mass in view of the dispersibility of the coloring material in the dispersion liquid. In addition, when at least two types of coloring materials are used in combination, the total mass thereof is preferably in the range described above.

Binder Resin 2

Although the binder resin is not particularly limited, a water soluble resin, such as a cellulose resin, a polyacrylic acid resin, a starch resin or an epoxy resin; or an organic solvent soluble resin, such as a polyacrylate resin, a polymethacrylate resin, a polystyrene resin, a polycarbonate resin, a poly(ether sulfone) resin, a poly(vinyl butyral) resin, an ethyl cellulose resin, an acetyl cellulose resin, a polyester resin, an AS resin, or a phenoxy resin may be preferably used. Those resins may be used alone, or if needed, at least two types thereof may be used in combination.

Surfactant

When a thermal head is heated, in order to impart a sufficient lubricity to the thermal transfer recording sheet of the present invention, a surfactant may be added thereto. As the surfactant, for example, a cationic surfactant, an anionic surfactant, or a nonionic surfactant may be mentioned.

As the cationic surfactant, for example, there may be mentioned dodecylammonium chloride, dodecylammonium bromide, dodecyltrimethylammonium bromide, dodecylpyridinium chloride, dodecylpyridinium bromide, or hexadecyltrimethylammonium bromide.

As the anionic surfactant, for example, there may be mentioned a fatty acid soap, such as sodium stearate or sodium dodecanoate; sodium dodecyl sulfate, sodium dodecylbenzene sulfate, or sodium lauryl sulfate.

As the nonionic surfactant, for example, there may be mentioned dodecyl polyoxyethylene ether, hexadecyl polyoxyethylene ether, nonylphenyl polyoxyethylene ether, lauryl polyoxyethylene ether, sorbitan monooleate polyoxyethylene ether, or monodecanoyl sucrose.

Wax 1

When a thermal head is not heated, in order to impart a sufficient lubricity to the thermal transfer recording sheet of the present invention, a wax may be added thereto. As a wax which may be added, although a polyethylene wax, a paraffin wax, or a fatty acid ester wax may be mentioned, the wax is not limited thereto.

Besides the above additives, if needed, for example, a UV absorber, an antiseptic agent, an antioxidant, an antistatic agent, and/or a viscosity modifier may also be added to the thermal transfer recording sheet of the present invention.

Medium 3

When the coloring material layer is formed, although a medium used to prepare a dispersion is not particularly limited, for example, water or an organic solvent may be mentioned. As the organic solvent, for example, there may be preferably mentioned an alcohol, such as methanol, ethanol, isopropyl alcohol, or isobutanol; a cellosolve, such as methyl cellosolve or ethyl cellosolve; an aromatic hydrocarbon, such as toluene, xylene, or chlorobenzene; an ester, such as ethyl acetate or butyl acetate; a ketone, such as acetone, methyl ethyl ketone, methyl isobutyl ketone, or cyclohexanone; a halogenated hydrocarbon, such as methylene chloride, chloroform, or trichloroethylene; an ether, such as tetrahydrofuran or dioxane; N,N-dimethylformamide, or N-methyl pyrrolidone. Those organic solvents may be used alone, or if needed, at least two thereof may be used in combination.

Substrate

Next, the substrate which forms the thermal transfer recording sheet will be described. The substrate functions to support the coloring material layer described above and is not particularly limited as long as having a heat resistance and a strength to some extent. A known material may be used for the substrate, and for example, there may be used a poly(ethylene terephthalate) film, a poly(ethylene naphthalate) film, a polycarbonate film, a polyimide film, a polyamide film, an aramid film, a polystyrene film, 1,4-polycyclohexylenedimethylene terephthalate film, a polysulfone film, a polypropylene film, a poly(phenylene sulfide) film, a poly(vinyl alcohol) film, a cellophane, a cellulose derivative, a polyethylene film, a poly(vinyl chloride) film, capacitor paper, or paraffin paper. Among those mentioned above, from a mechanical strength, a solvent resistance, and an economical point of view, a poly(ethylene terephthalate) film is preferable.

The thickness of the substrate is 0.5 to 50 μM and is preferably 3 to 10 μm in view of the transfer property.

When a dye ink is applied on the substrate to form the coloring material layer, the wettability and the adhesion of a coating liquid are liable to be insufficient. Hence, on the surface (forming surface) of the substrate on which the coloring material layer is to be formed, if needed, an adhesion treatment is preferably performed. The forming surface for the coloring material layer may be either one or two sides of the substrate. Although the adhesion treatment is not particularly limited, for example, there may be mentioned an ozone treatment, a corona discharge treatment, a UV treatment, a plasma treatment, a low-temperature plasma treatment, a primer treatment, or a chemical reagent treatment. In addition, those treatments may be performed in combination.

As the adhesion treatment on the substrate, an adhesion layer may be formed on the substrate by application. Although the adhesion layer is not particularly limited, for example, there may be used fine particles of an organic material, such as a polyester resin, a polystyrene resin, a polyacrylic acid ester resin, a polyamide resin, a polyether resin, a poly(vinyl acetate) resin, a polyethylene resin, a polypropylene resin, a poly(vinyl chloride) resin, a poly(vinyl alcohol) resin, or a poly(vinyl butyral) resin, or fine particles of an inorganic material, such as silica, alumina, magnesium carbonate, magnesium oxide, or titanium oxide.

Since including the compound represented by the general formula (1), the thermal transfer recording sheet of the present invention has a high chroma and also excellent dispersibility even under a high concentration condition.

Toner

Next, a toner according to the present invention will be described. Since having a high chroma and also excellent dispersibility even under a high concentration condition, the compound of the present invention is preferably used for a toner.

The toner of the present invention includes the compound represented by the general formula (1) as a colorant and a binder resin together with, if needed, a magnetic material, a wax, a charge controller, and other additives. As a method for manufacturing toner particles which form the toner of the present invention, for example, a pulverization method, a suspension polymerization method, a suspension granulation method, an emulsion polymerization method, or an emulsion aggregation method may be mentioned. Among those methods, the toner of the present invention in which the compound represented by the general formula (1) is used as a colorant is preferably a pulverized toner manufactured by a pulverization method.

In addition, although the compound represented by the general formula (1) used as the colorant may be used alone, at least two types thereof may also be used in combination. In addition, in accordance with the manufacturing method of toner, in order to adjust the color tone, a known pigment and/or dye may also be used together. Hereinafter, one example of the manufacturing method of a pulverized toner will be described.

Manufacturing Method of Pulverized Toner

The pulverized toner is manufactured in such a way that after the colorant and the like are uniformly dispersed in the binder resin by fusing and mixing, the fused and mixed product thus obtained is solidified by cooling and is then finely pulverized by a fine pulverizing machine, and the finely pulverized product thus obtained is sieved using a sieving machine to obtain toner particles having a desired particle diameter. In particular, first, the compound represented by the general formula (1) used as the colorant and the binder resin are sufficiently mixed together with, if needed, a magnetic material, a wax, a charge controller, and other additives by a mixing machine, such as a Henschel mixer or a ball mill. Next, by the use of a thermal mixing machine, such as a roll, a kneader, or an extruder, the mixture obtained as described above is sufficiently fused. Furthermore, by kneading and mixing, the resins are dissolved to each other and are then dispersed by addition of a wax and/or a magnetic material, if needed. In addition, after solidification is performed by cooling, pulverizing and sieving are performed, so that the pulverized toner can be obtained. For manufacturing of the pulverized toner, a known manufacturing machine, such as a mixing machine, a thermal mixing machine, and/or a sieving machine, can be used. Hereinafter, the components which form the toner will be described.

Colorant 3

As the colorant, the compound represented by the general formula (1) is used. As described above, the compound described above may be used alone, or at least two types thereof may be used in combination. In addition, if needed, a colorant, such as a known dye or pigment, may also be used together.

Although the colorant to be used together is not particularly limited, for example, there may be mentioned a condensed azo compound, an azo metal complex, a diketo pyrrolo pyrrole compound, an anthraquinone compound, a quinacridone compound, a naphthol compound, a benzimidazolon compound, a thioindigo compound, a perylene compound, a methine compound, an allylamide compound, and a base dye lake compound.

Binder Resin 3

As the binder resin used for the toner of the present invention, for example, a vinyl resin, a polyester resin, an epoxy resin, a polyurethane resin, a poly(vinyl butyral) resin, a terpene resin, a phenol resin, an aliphatic or an alicyclic hydrocarbon resin, or an aromatic petroleum resin may be mentioned, and furthermore, a rosin or a modified rosin may also be mentioned. Among those resins mentioned above, in view of charging property and fixability, a vinyl resin and a polyester resin are preferable, and a polyester resin is more preferably used since the charging property and the fixability are more effectively improved. Those resins may be used alone, or at least two types thereof may be used in combination. When at least two types of resins are used in combination, in order to control the viscoelastic properties of the toner, resins having different molecular weights are preferably mixed to each other.

The glass transition temperature (Tg) of the binder resin is preferably 45° C. to 80° C. and more preferably 55° C. to 70° C. In addition, the number average molecular weight (Mn) is preferably 1,500 to 50,000, and the weight average molecular weight (Mw) is preferably 6,000 to 1,000,000.

When a polyester resin is used as the binder resin, although the polyester resin is not particularly limited, the molar ratio of an alcohol component/an acid component among all the components is preferably 45/55 to 55/45. In the polyester resin, when the number of terminal groups of molecular chains is increased, the environmental dependence of the charging property of the toner is increased. Hence, the acid value is preferably 90 mgKOH/g or less and more preferably 50 mgKOH/g or less. In addition, the hydroxyl value is preferably 50 mgKOH/g or less and more preferably 30 mgKOH/g or less.

Wax 2

To the toner of the present invention, if needed, a wax may be added. As the wax, although a polyethylene wax, a paraffin wax, a fatty acid ester wax, or the like may be mentioned, the wax is not limited thereto.

Charge Controller 1

In addition, if needed, a charge controller may be mixed in the toner of the present invention. Although the charge controller is not particularly limited, as a controller which enables the toner to have a negative charge, for example, there may be mentioned a polymer or a copolymer having a sulfonic acid group, a sulfonic acid salt group, or a sulfonic acid ester group; a salicylic acid derivative or its metal complex; a monoazo metal compound; an acetylacetone metal compound; an aromatic oxy-carboxylic acid, an aromatic mono-carboxylic acid or an aromatic polycarboxylic acid or a metal salt, or an ester thereof; an aromatic poly-carboxylic acid anhydride; a phenol derivative, such as bisphenol A; a urea derivative, a metal-containing naphthoic acid compound, a boron compound, a quaternary ammonium salt, a calixarene, and a resin-based charge controller.

In addition, as a controller which enables the toner to have a positive charge, for example, there may be mentioned a nigrosine or a nigrosine-modified product formed of a fatty acid metal salt; a guanidine compound; an imidazole compound; a quaternary ammonium salt, such as tributylbenzylammonium-1-hydroxy-4-naphthosulfonic acid salt or tetrabutylammonium tetrafluoroborate; an onium salt, such as phosphonium, which is an analogue of the salt mentioned above or its lake pigment; a triphenylmethane dye or its lake pigment (as a laking agent, for example, phosphotungstic acid, phosphomolybdic acid, phosphotungstic molybdic acid, tannic acid, lauric acid, gallic acid, ferricyanide, or ferrocyanide may be mentioned); a metal salt of a higher fatty acid; a diorgano tin oxide, such as dibutyl tin oxide, dioctyl tin oxide, or dicyclohexyl tin oxide; a diorgano tin borate, such as dibutyl tin borate, dioctyl tin borate, or dicyclohexyl tin borate; or a resin-based charge controller. Those charge controllers may be used alone, or at least two types thereof may be used in combination.

Manufacturing Method of Liquid Developer

The toner of the present invention may also be used for a developer (hereinafter, referred to as "liquid developer") used for a liquid developing method. Hereinafter, a method for preparing a liquid developer using the toner of the present invention will be described.

The liquid developer can be obtained by dispersing or dissolving a coloring resin powder (toner) in an electric insulating carrier liquid together with, if needed, at least one additive, such as a charge controller and/or a wax. In addition, the liquid developer may also be prepared by a two-stage method in which a concentrated toner is formed in advance and is then diluted with an electric insulating carrier liquid.

Although a dispersing machine is not particularly limited, a medium type dispersing machine, such as a rotating shear type homogenizer, a ball mill, a sand mill, or an attritor, or a high-pressure counter collision type dispersing machine is preferably used.

Coloring Resin Powder

As the coloring resin powder, although the toner of the present invention is used, a colorant, such as a known pigment or dye, may also be further added. The number of types of colorants to be added may be one or more. As the colorant, the same material as described above by way of example as the constituent component of the toner may be mentioned.

Charge Controller 2

The charge controller may not be particularly limited as long as it has been used for a liquid developer for electrostatic development, and for example, there may be mentioned cobalt naphthenate, copper naphthenate, copper oleate, cobalt oleate, zirconium octylate, cobalt octylate, sodium dodecylbenzene sulfonate, calcium dodecylbenzene sulfonate, soy lecithin, or aluminum octoate.

Wax 3

AS the wax, the same wax as described above by way of example as the constituent component of the toner may be mentioned.

Electric Insulating Carrier Liquid

The electric insulating carrier liquid used in the present invention is not particularly limited, and for example, an organic solvent having a high electric resistance of $10^9$ Ω×cm or more and a low dielectric constant of 3 or less is preferably used. In particular, an aliphatic hydrocarbon solvent, such as hexane, pentane, octane, nonane, decane, undecane, or dodecane; Isopar H, G, K, L, or M (trade name, manufactured by Exxon Chemical Company, Inc.); or Linealene Dimer A-20 or A-20H (trade name, manufactured by Idemitsu Kosan Co., Ltd.), each of which has a boiling point of 68° C. to 250° C., is preferable. As long as the viscosity of the system is not increased, those solvents may be used alone, or at least two types thereof may be used in combination.

EXAMPLES

Hereinafter, although the present invention will be described in more detail with reference to examples and comparative examples, the present invention is not limited thereto. In addition, in the description, "part(s)" and "%" represent "part(s) by mass" and "percent by mass", respectively, unless otherwise particularly noted. In addition, the identification of an obtained compound was performed using a $^1$H nuclear magnetic resonance spectroscopic analysis ($^1$H-NMR) apparatus (ECA-400, manufactured by JEOL Ltd.) and an LC/TOF MS apparatus (LC/MSD TOF, manufactured by Agilent Technologies, Inc.).

Manufacturing Example 1: Manufacturing of Compound (1-1)

After 100 mg of p-toluene sulfonic acid was added to 20 mL of a toluene suspension liquid containing 10 mmol of the pyridone compound (B-1), the temperature was increased to 70° C., and 20 mL of a toluene solution containing 10 mmol of the aldehyde compound (A-1) was dripped. Subsequently, while azeotropic dehydration was performed, heating reflux was performed at 160° C. for 6 hours. After the reaction was completed, a reaction liquid was cooled to room temperature, and isopropyl alcohol was added thereto for dilution. After the reaction liquid was concentrated at a reduced pressure, the residue obtained thereby was purified using a column chromatography (eluent: ethyl acetate/heptane), so that 2.7 g (yield: 43%) of the compound (1-1) was obtained. The compound (1-1) was identified by a $^1$H-NMR analysis and a mass analysis.

Analytical Result of Compound (1-1)

[1] $^1$H-NMR (400 MHz, CDCl$_3$, room temperature): δ (ppm)=0.97 (6H, t, J–7.60 Hz), 1.36 (2H, dd, J=6.9 Hz), 1.54 (9H, m), 1.60-1.67 (4H, m), 2.37 (2H, s), 2.55 (2H, s), 3.46 (2H, br), 3.78 (2H, br), 7.14-7.28 (7H, m), 7.42 (1H, d, J=7.30 Hz), 7.60 (3H, t, J=18.5 Hz), 8.34 (1H, s)

[2] Mass analysis (ESI-TOF): m/z=624.3089 (M+H)$^+$

Manufacturing Example 2: Manufacturing of Compound (1-2)

Except that the aldehyde compound (A-2) and the pyridone compound (B-3) were used, the compound (1-2) was manufactured by a method similar to that of the manufacturing example 1 and then identified.

Analytical Result of Compound (1-2)

[1] $^1$H-NMR (400 MHz, CDCl$_3$, room temperature): δ (ppm)=0.90-1.02 (12H, m), 1.15 (9H, s), 1.15-1.28 (10H, m), 1.51 (9H, s), 1.57 (6H, s), 1.86 (1H, br), 2.04 (1H, br), 2.49 (3H, s), 3.41 (2H, br), 3.63-3.85 (2H, m), 7.34 (3H, dd, J=3.90, 9.80 Hz), 7.91 (2H, br), 8.27 (1H, s)

[2] Mass analysis (ESI-TOF): m/z=716.4571 (M+H)$^+$

Manufacturing Example 3: Manufacturing of Compound (1-5)

Except that the aldehyde compound (A-2) and the pyridone compound (B-2) were used, the compound (1-5) was manufactured by a method similar to that of the manufacturing example 1 and then identified.

Analytical Result of Compound (1-5)

[1] $^1$H-NMR (400 MHz, CDCl$_3$, room temperature): δ (ppm)=0.89-1.01 (12H, m), 1.24-1.42 (16H, m), 1.53-1.58 (11H, m), 2.07 (3H, s), 2.53 (3H, s), 3.42 (2H, br), 3.68-3.83 (2H, br), 7.30-7.39 (3H, m), 7.60-7.81 (2H, m), 8.31 (1H, s)

[2] Mass analysis (ESI-TOF): m/z=674.4120 (M+H)$^+$

Manufacturing Example 4: Manufacturing of Compound (1-8)

Except that the aldehyde compound (A-2) and the pyridone compound (B-1) were used, the compound (1-8) was manufactured by a method similar to that of the manufacturing example 1 and then identified.

Analytical Result of Compound (1-8)

[1] $^1$H-NMR (400 MHz, CDCl$_3$, room temperature): δ (ppm)=0.89-1.01 (12H, m), 1.27-1.49 (16H, m), 1.52 (9H, d, J=16.5 Hz), 1.90-2.01 (2H, m), 2.39 (1H, s), 2.56 (2H, s), 3.37 (2H, br), 3.74 (2H, br), 7.15-7.22 (4H, m), 7.26-7.29 (2H, m), 7.42 (2H, d, J=6.90 Hz), 7.55 (1H, d, J−7.30 Hz), 7.64 (1H, s), 8.34 (1H, s)

[2] Mass analysis (ESI-TOF): m/z=736.4290 (M+H)$^+$

Manufacturing Example 5: Manufacturing of Compound (1-9)

Except that the aldehyde compound (A-1) and the pyridone compound (B-3) were used, the compound (1-9) was manufactured by a method similar to that of the manufacturing example 1 and then identified.

Analytical Result of Compound (1-9)

[1] $^1$H-NMR (400 MHz, CDCl$_3$, room temperature): δ (ppm)=0.95-1.02 (6H, m), 1.16 (9H, s), 1.33-1.47 (4H, m), 1.51 (9H, s), 1.60-1.79 (4H, m), 2.49 (3H, s), 3.49 (2H, t, J=9.40 Hz), 3.78 (2H, t, J=9.8 Hz), 7.32-7.36 (3H, br), 7.86-7.94 (2H, br), 8.27 (1H, s)

[2] Mass analysis (ESI-TOF): m/z=604.4263 (M+H)$^+$

Manufacturing Example 6: Manufacturing of Compound (1-11)

Except that the aldehyde compound (A-5) and the pyridone compound (B-3) were used, the compound (1-11) was manufactured by a method similar to that of the manufacturing example 1 and then identified.

Analytical Result of Compound (1-11)

[1] $^1$H-NMR (400 MHz, CDCl$_3$, room temperature): δ (ppm)=0.87-1.03 (12H, m), 1.16 (9H, s), 1.24-1.59 (15H, m), 1.90 (1H, s), 2.04 (1H, s), 2.19 (3H, s), 3.44 (2H, br), 3.80 (2H, br), 7.38 (3H, br), 7.50-7.61 (5H, m), 7.78 (2H, s), 7.92 (2H, br)

[2] Mass analysis (ESI-TOF): m/z=736.4271 (M+H)$^+$

Manufacturing Example 7: Manufacturing of Compound (1-17)

Except that the aldehyde compound (A-7) and the pyridone compound (B-1) were used, the compound (1-17) was manufactured by a method similar to that of the manufacturing example 1 and then identified.

Analytical Result of Compound (1-17)

[1] $^1$H-NMR (400 MHz, CDCl$_3$, room temperature): δ (ppm)=0.87-1.03 (6H, m), 1.25-1.59 (3H, m), 1.6-1.68 (3H, m), 1.80-1.92 (2H, m), 2.01 (3H, s), 2.01 (3H, s), 3.55 (2H, br), 3.81 (2H, br), 7.15-7.27 (6H, m), 7.30-7.31 (2H, m), 7.42-7.44 (2H, m), 7.56-7.58 (2H, m)

[2] Mass analysis (ESI-TOF): m/z=672.3281 (M+H)$^+$

Manufacturing Example 8: Manufacturing of Compound (1-18)

Except that the aldehyde compound (A-11) and the pyridone compound (B-2) were used, the compound (1-18) was manufactured by a method similar to that of the manufacturing example 1 and then identified.

Analytical Result of Compound (1-18)

[1] $^1$H-NMR (400 MHz, CDCl$_3$, room temperature): δ (ppm)=0.87-1.08 (6H, m), 1.34-1.68 (4H, m), 1.80-1.96 (4H, m), 2.10 (3H, s), 3.54 (2H, br), 3.76 (6H, s), 3.84 (2H, br), 6.68 (3H, t, J=7.80 Hz), 7.17-7.31 (4H, m), 7.42-7.44 (3H, m), 7.53-7.68 (4H, m)

[2] Mass analysis (ESI-TOF): m/z=704.3192 (M+H)$^+$

Manufacturing Example 9: Manufacturing of Compound (1-19)

Except that the aldehyde compound (A-12) and the pyridone compound (B-1) were used, the compound (1-19) was manufactured by a method similar to that of the manufacturing example 1 and then identified.

Analytical Result of Compound (1-19)

[1] $^1$H-NMR (400 MHz, CDCl$_3$, room temperature): δ (ppm)=0.92 (3H, t, J=7.10 Hz), 1.07 (3H, t, J=5.50 Hz), 1.31 (2H, br), 1.52 (2H, br), 1.68 (2H, br), 1.84 (2H, br), 1.92 (2H, br), 1.94 (3H, s), 1.95 (6H, s), 2.07 (3H, s), 2.17 (3H, s), 2.25 (3H, s), 2.30 (3H, s), 3.59 (2H, br), 3.79-3.83 (2H, s), 7.26-7.43 (4H, m), 7.61-7.82 (2H, m)

[2] Mass analysis (ESI-TOF): m/z=652.3685 (M+H)$^+$

Manufacturing of Ink

By the following method, an ink of the present invention and a comparative ink were manufactured.

Example 1: Manufacturing of Ink (1)

An ink (1) was obtained by mixing 5 parts of the compound (1-1) synthesized in the manufacturing example 1, 350 parts of toluene, 350 parts of ethyl acetate, and 300 parts of methyl ethyl ketone.

Examples 2 to 9: Manufacturing of Inks (2) to (9)

In Example 1, except that the compound (1-1) was changed to the compounds shown in Table 1, inks (2) to (9) were manufactured by a method similar to that of Example 1.

Comparative Examples 1 to 4: Manufacturing of Comparative Inks (1) to (4)

In Example 1, except that the compound (1-1) was changed to the following comparative compounds (C-1) to (C-4), comparative inks (1) to (4) were manufactured by a method similar to that of Example 1.

[Chem. 8]

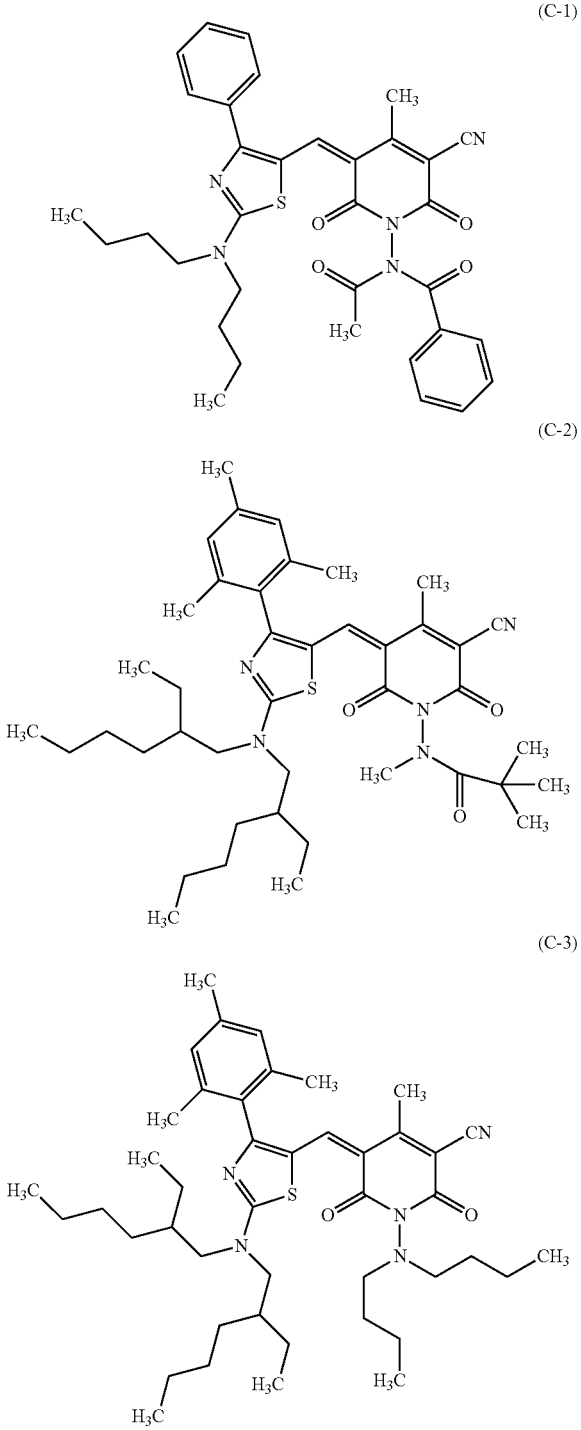

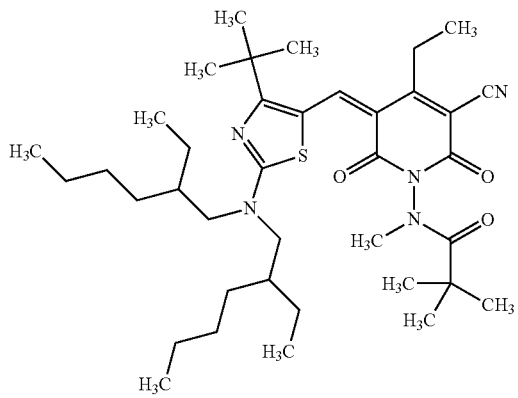

Formation of Image Sample 1

After the inks (1) to (9) and the comparative inks (1) to (4) manufactured as described above were each applied on a hiding-chart by a bar coating method (Bar No. 10), air drying thereof was performed over one night, so that image samples were obtained.

Evaluation of Chroma 1

The chromaticity (L*, a*, b*) of the L*a*b* color system of each image sample thus formed was measured using a reflection densitometer SpectroLino (manufactured by Gretag Macbeth Inc.), and the chroma (C*) was calculated by the following formula.

$$C^* = \sqrt{(a^*)^2 + (b^*)^2} \qquad [\text{Math. 1}]$$

As the chroma C* and the lightness L* are both larger, the extension of chroma becomes preferable, so that a high chroma is obtained. The results are shown in Table 1.

In addition, the evaluation criteria are as follows.

A: L* is 50.0 or more, and C* is 85.0 or more.

B: L* is 40.0 to less than 50.0, and C* is 85.0 or more.

C: L* is less than 40.0, or C* is less than 85.0.

Evaluation of Dispersibility 1

Next, by the use of a phase-contrast microscope (BX53, manufactured by Olympus Corp.), the image samples described above were each observed at a magnification of 20 times, so that the dispersibility of the compound was evaluated. The colorant of the ink used for forming each image sample was in a high concentration state as compared to that of a general ink. The results are shown in Table 1.

In addition, the evaluation criteria are as follows.

A: Aggregates of the compound are hardly confirmed.

B: Aggregates of the compound are slightly confirmed.

C: Aggregates of the compound are fairly confirmed.

TABLE 1

|  | Compound | Ink | C* | L* | Evaluation of Chroma | Evaluation of Dispersibility |
| --- | --- | --- | --- | --- | --- | --- |
| Example 1 | Compound (1-1) | Ink (1) | 88.6 | 54.9 | A | A |
| Example 2 | Compound (1-2) | Ink (2) | 89.1 | 55.3 | A | A |
| Example 3 | Compound (1-5) | Ink (3) | 89.9 | 55.0 | A | A |
| Example 4 | Compound (1-8) | Ink (4) | 89.5 | 55.7 | A | A |

TABLE 1-continued

|  | Compound | Ink | C* | L* | Evaluation of Chroma | Evaluation of Dispersibility |
|---|---|---|---|---|---|---|
| Example 5 | Compound (1-9) | Ink (5) | 87.9 | 54.0 | A | A |
| Example 6 | Compound (1-11) | Ink (6) | 98.2 | 47.8 | B | A |
| Example 7 | Compound (1-17) | Ink (7) | 88.3 | 56.9 | A | A |
| Example 8 | Compound (1-18) | Ink (8) | 85.8 | 56.9 | A | A |
| Example 9 | Compound (1-19) | Ink (9) | 85.2 | 84.8 | A | A |
| Comparative Example 1 | Comparative Compound (C-1) | Comparative Ink (1) | 79.9 | 37.1 | C | C |
| Comparative Example 2 | Comparative Compound (C-2) | Comparative Ink (2) | 89.7 | 49.0 | B | C |
| Comparative Example 3 | Comparative Compound (C-3) | Comparative Ink (3) | 83.6 | 54.3 | C | C |
| Comparative Example 4 | Comparative Compound (C-4) | Comparative Ink (4) | 84.4 | 48.4 | C | B |

As shown in Table 1, it was found that the inks of the examples each containing the compound represented by the general formula (1) had a high chroma and also excellent dispersibility even under a high concentration condition as compared to those of the comparative inks.

Manufacturing of Color Filter

By the following methods, a resist composition for a color filter and a color filter were manufactured.

Example 10

After 12 parts of the compound (1-1) synthesized in the manufacturing example 1 was mixed with 120 parts of cyclohexane, the mixture thus obtained was dispersed for 1 hour using an attritor (manufactured by Mitsui Mining Co., Ltd.), so that a resist composition ink (1) was obtained.

Subsequently, to a solution containing 6.7 parts of an acrylic copolymer composition (weight average molecular weight Mw: 10,000) formed from 40 percent by mass of n-butyl methacrylate, 30 percent by mass of acrylic acid, and 30 percent by mass of hydroxyethyl methacrylate on a molar ratio basis; 1.3 parts of dipentaerythritol pentaacrylate; 0.4 parts of 2-benzyl-2-dimethylamino-1-(4-morpholinophenyl)-butanone (photopolymerization initiator); and 96 parts of cyclohexane, 22 parts of the above resist composition ink (1) was slowly added and was then stirred at room temperature for 3 hours. The mixture thus obtained was filtrated using 1.5-μm filter, so that a resist composition (1) was obtained.

After the resist composition (1) described above was spin-coated on a glass substrate and was then dried at 90° C. for 3 minutes, the entire surface thereof was exposed and then post-cured at 180° C., so that a color filter (1) was formed.

Examples 11 to 14

In Example 10, except that the compound (1-1) was changed to the compounds shown in Table 2, resist compositions (2) to (5) were obtained by a method similar to that of Example 10. In addition, except that the resist compositions (2) to (5) were used instead of using the resist composition (1), color filters (2) to (5) were formed by a procedure similar to that of Example 10.

Comparative Examples 5 to 8

In Example 10, except that the compound (1-1) was changed to the compounds (C-1) to (C-4), comparative resist compositions (1) to (4) were obtained by a method similar to that of Example 10. In addition, except that the comparative resist compositions (1) to (4) were used instead of using the resist composition (1), comparative color filters (1) to (4) were formed by a procedure similar to that of Example 10.

Evaluation of Chroma 2

The chromaticity (L*, a*, b*) of the L*a*b* color system of each color filter was measured using a reflection densitometer SpectroLino (manufactured by Gretag Macbeth Inc.), and the chroma (C*) was calculated by the formula described above. The results are shown in Table 2.

In addition, the evaluation criteria are as follows.

A: L* is 50.0 or more, and C* is 85.0 or more.

B: L* is 40.0 to less than 50.0, and C* is 85.0 or more.

C: L* is less than 40.0, or C* is less than 85.0.

Evaluation of Dispersibility 2

Next, by the use of a phase-contrast microscope (BX53, manufactured by Olympus Corp.), the color filters described above were each observed at a magnification of 20 times, so that the dispersibility of the compound was evaluated. The results are shown in Table 2.

In addition, the evaluation criteria are as follows.

A: Aggregates of the compound are hardly confirmed.

B: Aggregates of the compound are slightly confirmed.

C: Aggregates of the compound are fairly confirmed.

TABLE 2

|  | Compound | Application | C* | L* | Evaluation of Chroma | Evaluation of Dispersibility |
|---|---|---|---|---|---|---|
| Example 10 | Compound (1-1) | Color Filter (1) | 88.1 | 55.1 | A | A |
| Example 11 | Compound (1-2) | Color Filter (2) | 88.9 | 55.2 | A | A |
| Example 12 | Compound (1-11) | Color Filter (3) | 98.4 | 48.0 | B | A |
| Example 13 | Compound (1-17) | Color Filter (4) | 88.5 | 57.3 | A | A |
| Example 14 | Compound (1-18) | Color Filter (5) | 86.1 | 57.0 | A | A |

TABLE 2-continued

|  | Compound | Application | C* | L* | Evaluation of Chroma | Evaluation of Dispersibility |
|---|---|---|---|---|---|---|
| Comparative Example 5 | Comparative Compound (C-1) | Comparative Color Filter (1) | 79.5 | 37.1 | C | C |
| Comparative Example 6 | Comparative Compound (C-2) | Comparative Color Filter (2) | 89.1 | 48.8 | B | C |
| Comparative Example 7 | Comparative Compound (C-3) | Comparative Color Filter (3) | 83.2 | 54.2 | C | C |
| Comparative Example 8 | Comparative Compound (C-4) | Comparative Color Filter (4) | 84.2 | 48.1 | C | B |

Manufacturing of Thermal Transfer Recording Sheet

By the following method, a thermal transfer recording sheet was manufactured.

Example 15

To a solution in which 13.5 parts of the compound (1-1) synthesized in the manufacturing example 1 was dissolved in 90 parts of a mixed solvent containing methyl ethyl ketone and toluene at a ratio of 1:1, 15 parts of a poly(vinyl butyral) resin (Denka 3000-K, manufactured by Denki Kagaku Kogyo K.K.) was gradually added with stirring, so that a thermal transfer recording sheet ink (1) was formed.

The above thermal transfer recording sheet ink (1) was applied on a poly(ethylene terephthalate) film (Lumirror (registered trade name), manufactured by Toray Industries, Inc.) having a thickness of 4.5 μm to have a thickness of 1 μm after drying and then dried, so that a thermal transfer recording sheet (1) was formed.

Examples 16 to 19

In Example 15, except that the compound (1-1) was changed to the compounds shown in Table 3, thermal transfer recording sheets (2) to (5) were each formed by a method similar to that of Example 15.

Comparative Examples 9 to 12

In Example 15, except that the compound (1-1) was changed to the above comparative compounds (C-1) to (C-4), comparative thermal transfer recording sheets (1) to (4) were formed by a method similar to that of Example 15.

Formation of Image Sample 2

The thermal transfer recording sheets (1) to (5) and the comparative thermal transfer recording sheets (1) to (4) were each transferred on printing paper using a modified photoprinter SELPHY manufactured by CANON KABUSHIKI KAISHA, so that image samples were formed.

Evaluation of Chroma 3

The chromaticity (L*, a*, b*) of the L*a*b* color system of each image sample was measured using a reflection densitometer SpectroLino (manufactured by Gretag Macbeth Inc.), and the chroma (C*) was calculated by the formula described above. The results are shown in Table 3.

In addition, the evaluation criteria are as follows.
A: L* is 50.0 or more, and C* is 85.0 or more.
B: L* is 40.0 to less than 50.0, and C* is 85.0 or more.
C: L* is less than 40.0, or C* is less than 85.0.

Evaluation of Dispersibility 3

Next, by the use of a phase-contrast microscope (BX53, manufactured by Olympus Corp.), the image samples described above were each observed at a magnification of 20 times, so that the dispersibility of the compound was evaluated. The results are shown in Table 3.

In addition, the evaluation criteria are as follows.
A: Aggregates of the compound are hardly confirmed.
B: Aggregates of the compound are slightly confirmed.
C: Aggregates of the compound are fairly confirmed.

TABLE 3

|  | Compound | Application | C* | L* | Evaluation of Chroma | Evaluation of Dispersibility |
|---|---|---|---|---|---|---|
| Example 15 | Compound (1-1) | Thermal Transfer Sheet (1) | 88.2 | 54.1 | A | A |
| Example 16 | Compound (1-5) | Thermal Transfer Sheet (2) | 89.5 | 55.1 | A | A |
| Example 17 | Compound (1-9) | Thermal Transfer Sheet (3) | 87.1 | 53.8 | B | A |
| Example 18 | Compound (1-17) | Thermal Transfer Sheet (4) | 88.2 | 56.7 | A | A |
| Example 19 | Compound (1-19) | Thermal Transfer Sheet (5) | 85.1 | 84.8 | A | A |
| Comparative Example 9 | Comparative Compound (C-1) | Comparative Thermal Transfer Sheet (1) | 78.9 | 36.8 | C | C |
| Comparative Example 10 | Comparative Compound (C-2) | Comparative Thermal Transfer Sheet (2) | 88.8 | 49.5 | B | C |
| Comparative Example 11 | Comparative Compound (C-3) | Comparative Thermal Transfer Sheet (3) | 83.7 | 55.1 | C | C |
| Comparative Example 12 | Comparative Compound (C-4) | Comparative Thermal Transfer Sheet (4) | 84.0 | 48.5 | C | B |

Manufacturing of Toner

By the following method, a toner was manufactured.

Example 20

Binder resin (polyester resin): 100 parts by mass
(Tg: 55° C., acid value: 20 mgKOH/g, hydroxy value: 16 mgKOH/g, molecular weights Mp: 4,500, Mn: 2,300, and Mw: 38,000)
Compound (1-1): 5 parts by mass
1,4-di-t-butylsalycilic acid aluminum compound 0.5 parts by mass Paraffin wax (maximum endothermic peak temperature: 78° C.) 5 parts by mass After the above materials were sufficiently mixed together using a Henschel mixer (FM-75J type, manufactured by Mitsui Mining Co., Ltd.), mixing was performed by a double-screw extruder (PCM-45 type, manufactured by Ikegai Ironworks Corp.) which was set at a temperature of 130° C. and at a feed amount of 60 kg/hr (the temperature of a mixed product at an extrusion stage was approximately 150° C.). After the mixed product thus obtained was cooled and then coarsely pulverized by a hammer mill, fine pulverization was performed at a feed amount of 20 kg/hr using a mechanical pulverizer (T-250, manufactured by Turbo Kogyo Co., Ltd.). Furthermore, the finely pulverized product thus obtained was sieved by a multistage sieving machine using a Coanda effect, so that toner particles were obtained. To 100 parts by mass of the toner particles thus obtained, 2 parts by mass of silica fine particles was externally added using a Henschel mixer, so that a toner (1) was obtained. The weight average particle diameter (D4) of the toner (1) thus obtained was approximately 6.1 μm, the rate of particles having a particle diameter of 4.0 arm or less was 30.5% in number, and the rate of particles having a particle diameter of 10.1 μm or more was 0.7% in volume.

Examples 21 to 27

In Example 20, except that the compound (1-1) was changed to the compounds shown in Table 4, toners (2) to (8) were manufactured by a method similar to that of Example 20.

Comparative Examples 13 to 16

In Example 20, except that the compound (1-1) was changed to the above comparative compounds (C-1) to (C-4), comparative toners (1) to (4) were manufactured by a method similar to that of Example 20.

Formation of Image Sample 3

By the use of the toners (1) to (8) and the comparative toners (1) to (4), image samples were output, and the image characteristics which will be described below were compared to each other. In addition, as an image forming apparatus, a modified LBP-5300 (manufactured by CANON KABUSHIKI KAISHA) was used. As the modification of the apparatus, a developing blade in a process cartridge (hereinafter, abbreviated as "CRG") was changed to a SUS blade having a thickness of 8 mm. In addition, the apparatus was configured so that a blade bias of −200 V could be applied with respect to a development bias applied to a developing roller which was a toner carrier. Upon the evaluation, a CRG in which a yellow toner was filled was prepared for each evaluation item.

Evaluation of Chroma 4

The evaluation of chroma was performed as described below. In a normal environment (temperature of 25° C./humidity of 60% RH), a fixed image having a bearing amount of 0.45 mg/cm$^2$ was formed on a CLC color copy sheet (manufactured by CANON KABUSHIKI KAISHA). The chromaticity (L*, a*, b*) of the L*a*b* color system of each fixed image thus obtained was measured using a reflection densitometer SpectroLino (manufactured by Gretag Macbeth Inc.), and the chroma (C*) was calculated by the formula described above. The results are shown in Table 4.

In addition, the evaluation criteria are as follows.
A: L* is 50.0 or more, and C* is 85.0 or more.
B: L* is 40.0 to less than 50.0, and C* is 85.0 or more.
C: L* is less than 40.0, or C* is less than 85.0.

Evaluation of Dispersibility 4

Next, by the use of a phase-contrast microscope (BX53, manufactured by Olympus Corp.), the fixed images described above were each observed at a magnification of 20 times, so that the dispersibility of the compound was evaluated. The results are shown in Table 4.

In addition, the evaluation criteria are as follows.
A: Aggregates of the compound are hardly confirmed.
B: Aggregates of the compound are slightly confirmed.
C: Aggregates of the compound are fairly confirmed.

TABLE 4

| | Compound | Application | C* | L* | Evaluation of Chroma | Evaluation of Dispersibility |
|---|---|---|---|---|---|---|
| Example 20 | Compound (1-1) | Toner (1) | 87.8 | 54.0 | A | A |
| Example 21 | Compound (1-5) | Toner (2) | 87.0 | 53.4 | A | A |
| Example 22 | Compound (1-8) | Toner (3) | 88.9 | 54.9 | A | A |
| Example 23 | Compound (1-9) | Toner (4) | 87.0 | 105.0 | A | A |
| Example 24 | Compound (1-11) | Toner (5) | 97.2 | 46.5 | B | A |
| Example 25 | Compound (1-17) | Toner (6) | 87.9 | 55.6 | A | A |
| Example 26 | Compound (1-18) | Toner (7) | 85.1 | 56.1 | A | A |
| Example 27 | Compound (1-19) | Toner (8) | 85.0 | 83.9 | A | A |
| Comparative Example 13 | Comparative Compound (C-1) | Comparative Toner (1) | 50.2 | 35.6 | C | C |
| Comparative Example 14 | Comparative Compound (C-2) | Comparative Toner (2) | 63.3 | 48.1 | B | C |
| Comparative Example 15 | Comparative Compound (C-3) | Comparative Toner (3) | 83.1 | 53.2 | C | C |
| Comparative Example 16 | Comparative Compound (C-4) | Comparative Toner (4) | 82.5 | 47.2 | C | B |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A compound represented by the following formula (1),

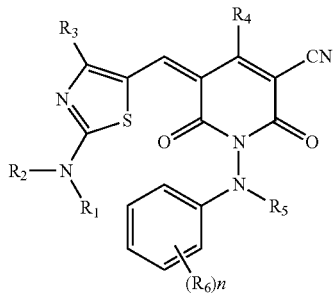

wherein in the formula (1), $R_1$ and $R_2$ each independently represent a substituted or an unsubstituted alkyl group, $R_3$ represents an unsubstituted alkyl group or a substituted or an unsubstituted aryl group, $R_4$ represents an unsubstituted alkyl group, $R_5$ represents a substituted or an unsubstituted alkyl group, a substituted or an unsubstituted aryl group, or a substituted or an unsubstituted acyl group, $R_6$ represents an unsubstituted alkyl group or an alkoxy group, and n represents an integer of 0 to 5, wherein when n is an integer of 2 to 5, a plurality of $R_6$'s are the same or different from each other.

2. The compound according to claim 1, wherein $R_3$ in the formula (1) represents a tert-butyl group.

3. An ink comprising: a medium; and a compound dispersed in the medium, wherein the compound is the compound according to claim 1.

4. A resist composition for a color filter comprising: the compound according to claim 1.

5. A thermal transfer recording sheet comprising: a substrate; and a coloring material layer formed thereon, wherein the coloring material layer contains the compound according to claim 1.

6. A toner comprising: a binder resin; and a colorant, wherein the colorant contains the compound according to claim 1.

* * * * *